United States Patent

Meyer et al.

Patent Number: 6,136,225
Date of Patent: Oct. 24, 2000

[54] POLYMERIZABLE LIQUID-CRYSTALLINE COMPOUNDS

[75] Inventors: Frank Meyer, Ludwigshafen; Karl Siemensmeyer, Frankenthal; Karl-Heinz Etzbach, Frankenthal; Peter Schuhmacher, Mannheim, all of Germany

[73] Assignee: BASF Aktiengesellschaft, Ludwigshafen, Germany

[21] Appl. No.: 09/029,068

[22] PCT Filed: Aug. 26, 1996

[86] PCT No.: PCT/EP96/03756

§ 371 Date: Mar. 2, 1998

§ 102(e) Date: Mar. 2, 1998

[87] PCT Pub. No.: WO97/00600

PCT Pub. Date: Jan. 9, 1997

[30] Foreign Application Priority Data

Sep. 1, 1995 [DE] Germany .................... 195 32 408

[51] Int. Cl.[7] .......................... C09K 19/20; C09K 19/38; C07C 69/76; C07C 261/00; C09D 5/00; C08F 26/02

[52] U.S. Cl. ................. 252/299.01; 252/299.64; 252/299.67; 106/401; 560/24; 560/95; 560/115; 564/188; 526/301; 526/302

[58] Field of Search ............... 252/299.01, 299.61, 252/299.63, 299.64, 299.65, 299.66, 299.67; 106/400, 401, 500, 505; 560/24, 115, 95; 564/47, 52, 188

[56] References Cited

U.S. PATENT DOCUMENTS 5,798,147  8/1998  Beck et al. .................. 427/511
5,833,880  11/1998  Siemensmeyer et al. ......... 252/299.64

FOREIGN PATENT DOCUMENTS 643121   3/1995  European Pat. Off. .
2609999  7/1988  France .
4226994  2/1994  Germany .
4405316  8/1995  Germany .
4408170  9/1995  Germany .
9408268  4/1994  WIPO .

*Primary Examiner*—Shean C. Wu
*Attorney, Agent, or Firm*—Oblon, Spivak, McClelland, Maier & Neustadt, P.C.

[57] ABSTRACT

Polymerizable liquid-crystalline compounds of the formula I $$Z^1-Y^1-A^1-Y^3-M-Y^4-A^2-Y^2-Z^2 \qquad I$$

where $Z^1$ and $Z^2$ are radicals containing reactive groups via which polymerization can be effected, $Y^1-Y^4$ are a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups $Y^3$ and $Y^4$ is —O—CO—O—, —O—CO—NR—, —NR—CO—O— or —NR—CO—NR—, $A^1$ and $A^2$ are spacers having 2 to 30 carbon atoms in which the carbon chain may be interrupted by ether oxygen, thioether sulfur or by nonadjacent imino or $C_1$–$C_4$-alkylimino groups, M is a mesogenic group, R is $C_1$–$C_4$-alkyl, and compositions comprising them are distinguished by favorable liquid-crystalline phase-temperature ranges and can be used in optical display devices and in cholesteric liquid-crystalline colorants.

19 Claims, No Drawings

POLYMERIZABLE LIQUID-CRYSTALLINE COMPOUNDS

BACKGROUND OF THE INVENTION

This application is a 371 of PCT/EP96/03756, filed Aug. 26, 1996.

1. Field of the Invention

The present invention relates to novel polymerizable liquid-crystalline compounds of the formula I $$Z^1-Y^1-A^1-Y^3-M-Y^4-A^2-Y^2-Z^2 \qquad I$$

where

- $Z^1$ and $Z^2$ are radicals containing reactive groups via which polymerization can be effected,
- $Y^1-Y^4$ are a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups $Y^3$ and $Y^4$ is —O—CO—O—, —O—CO—NR—, —NR—CO—O— or —NR—CO—NR—,
- $A^1$ and $A^2$ are spacers having 2 to 30 carbon atoms in which the carbon chain may be interrupted by ether oxygen, thioether sulfur or by nonadjacent imino or $C_1-C_4$-alkylimino groups,
- M is a mesogenic group,
- R is $C_1-C_4$-alkyl.

The present invention furthermore relates to liquid-crystal compositions comprising these compounds and possibly one or more chiral compounds, to a process for preparing the novel liquid-crystalline compounds, to a process for coating substrates with the novel compounds or liquid-crystal compositions, and to the use of the compounds or liquid-crystal compositions for producing optical display devices, as cholesteric liquid-crystalline colorants, and to pigments obtainable by polymerizing the liquid-crystal compositions and subsequently comminuting.

2. Description of the Background

Numerous compounds are not converted directly into the liquid, unordered state on warming from the crystalline state with a defined close and long-distance ordering of the molecules, but instead pass through a liquid-crystalline phase, in which, although the molecules are mobile, the molecule axes form an ordered structure. Elongate molecules frequently form nematic liquid-crystalline phases which are characterized by an alignment long-distance ordering owing to parallel arrangement of the long axes of the molecules. If a nematic phase of this type contains chiral compounds, a so-called cholesteric phase forms, which is characterized by a helical superstructure of the long axes of the molecules. The chiral compound here can be the liquid-crystalline compound itself or it can be added to a nematic liquid-crystalline phase as a chiral dope.

Liquid-crystalline materials have remarkable optical properties based on thier anisotropic ordered state. However, the liquid-crystalline ordered state only occurs in a limited temperature range. The temperature range in which liquid-crystalline phases occur is frequently far above the desired use temperature or extends only over a small temperature range.

There are various ways of obtaining and fixing the ordering structures desired for the material properties, even in the solid state. In addition to glass-like solidification on cooling from the liquid-crystalline state, there is also the possibility of copolymerization into polymeric networks or, if the liquid-crystalline compounds contain polymerizable groups, polymerization of the liquid-crystalline compounds themselves.

Polymerizable liquid-crystalline compounds are described, for example, in EP-A 261 712 and in WO 93/05436, WO 95/24453, WO 95/24454 and WO 95/24455. In polymeric form, these compounds usually have the requisite mechanical stabilities, but are in some cases unsatisfactory owing to the temperature level of their liquid-crystalline phases and the temperature range of these phases.

SUMMARY OF THE INVENTION

It is an object of the present invention to provide polymerizable liquid-crystalline compounds or liquid-crystal compositions which have low liquid-crystalline phase temperatures, broad liquid-crystalline phase ranges and, in the polymeric state, good mechanical strength and fixing of the liquid-crystalline ordered state.

We have found that this object is achieved by the polymerizable liquid-crystalline compounds and liquid-crystal compositions comprising the latter described at the outset.

DETAILED DESCRIPTION OF THE INVENTION

For the purposes of the present invention, polymerization is taken to mean all reactions in which polymers are built up, ie. addition polymerization as a chain reaction, addition polymerization as a stepwise reaction and condensation polymerization.

Preferred radicals $Z^1$ and $Z^2$ are the following:

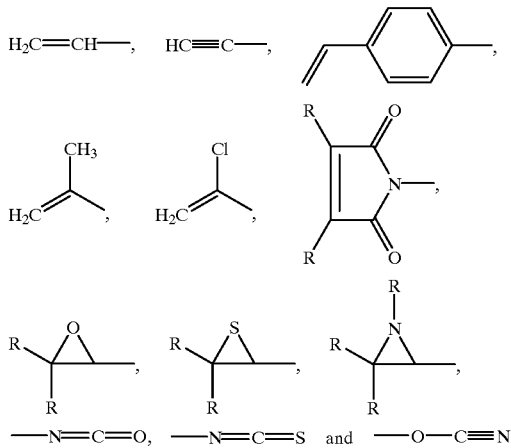

where the radicals R are identical or different $C_1-C_4$-alkyl.

Of the reactive polymerizable groups, the cyanates can trimerize spontaneously to form cyanurates and are therefore preferred. Polymerization of compounds containing epoxide, thiirane, aziridine, isocyanate and isothiocyanate groups requires further compounds containing complementary reactive groups. For example, isocyanates can polymerize with alcohols to form urethanes and with amines to form urea derivatives. An analogous situation applies to thiiranes and aziridines. The complementary reactive groups can either be present in a second novel compound, which is mixed with the first, or they can be introduced into the polymerization mixture by means of auxiliary compounds containing two or more of these complementary groups. If these compounds in each case contain two of these reactive groups, linear polymers having a predominantly thermoplastic character are formed. If the compounds contain more than two reactive groups, crosslinked polymers which are particularly mechanically stable are formed. The maleimido group is particularly suitable for free-radical copolymerization with olefinic compounds such as styrene.

Preferred polymerizable groups $Z^1$ and $Z^2$ are those which are susceptible to free-radical polymerization, ie. in particular olefinically unsaturated groups, and of these the groups

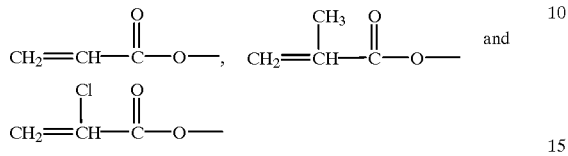

are of particular importance in combination with $Y^1$ and $Y^2$.

The moieties $Z^1$, $Z^2$, $A^1$, $A^2$, M and X in the novel compounds are linked to one another via bridges $Y^1$–$Y^4$, such as —O—, —S—, —CO—O—, —O—CO—, —O—CO—O—, —CO—NR—, —NR—CO—, —O—CO—NR—, —NR—CO—O—, —NR—CO—NR—, or alternatively via a direct bond, where at least one link of the spacer $A^1$ or $A^2$ to the mesogenic group is via a carbonate group (—OCOO—), a carbamate group (—O—CO—NR— or —NR—CO—O—) or a urea group (—NR—CO—NR—). Chiral polymerizable compounds containing one of these groups have the advantageous property of particularly low phase-transition temperatures and broad phase ranges and are thus particularly suitable for applications at room temperature. This is particularly true of the carbonate group.

Suitable spacers $A^1$ and $A^2$ are all groups known for this purpose. The spacers generally contain from 2 to 30, preferably 3 to 12, carbon atoms and comprise predominantly linear aliphatic groups. They can be interrupted in the chain by, for example, nonadjacent oxygen or sulfur atoms or imino or alkylimino groups, such as methylimino groups. Suitable substituents for the spacer chain are furthermore fluorine, chlorine, bromine, cyano, methyl and ethyl.

Examples of representative spacers are the following:

—$(CH_2)_p$—, —$(CH_2CH_2O)_mCH_2CH_2$—, —$CH_2CH_2SCH_2CH_2$—, —$CH_2CH_2NHCH_2CH_2$—,

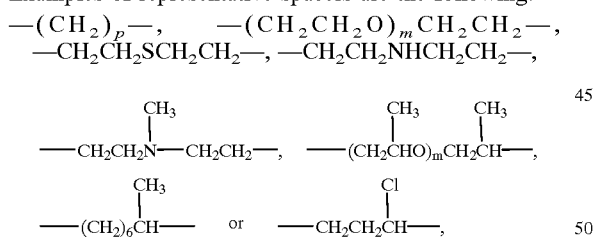

where m is from 1 to 3, and p is from 1 to 12.

The radicals M can be any known mesogenic groups. Particularly suitable groups are those of the formula Ia —(—T—$Y^5$—)$_r$—T—          Ia where T is a divalent saturated or unsaturated iso- or heterocyclic radical, $Y^5$ is a bridge as defined for $Y^1$–$Y^4$; —$CH_2$—O—; —O—$CH_2$—; —CH=N—; —N=CH— or —N=N—, r is 0, 1, 2 or 3, where the radicals T and $Y^5$, in the case where r is >0, may be identical or different.

r is preferably 1 or 2.

The radicals T can also be ring systems substituted by fluorine, chlorine, bromine, cyano, hydroxyl or nitro. Preferred radicals T are the following:

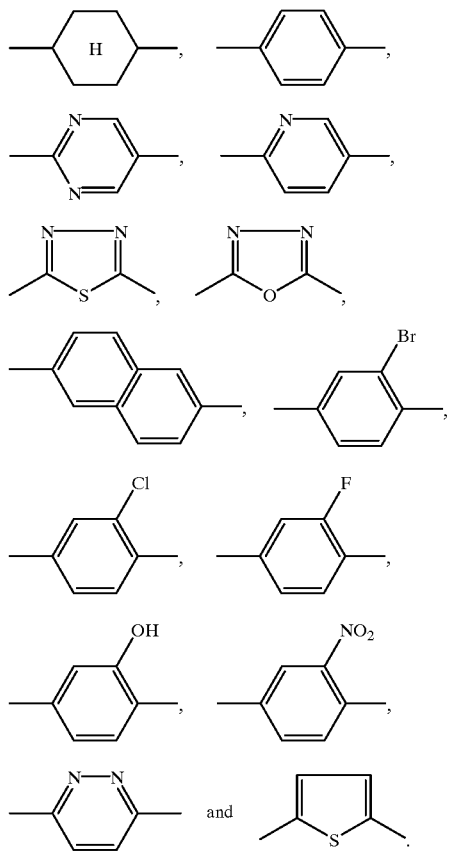

Examples of preferred mesogenic groups M are the following:

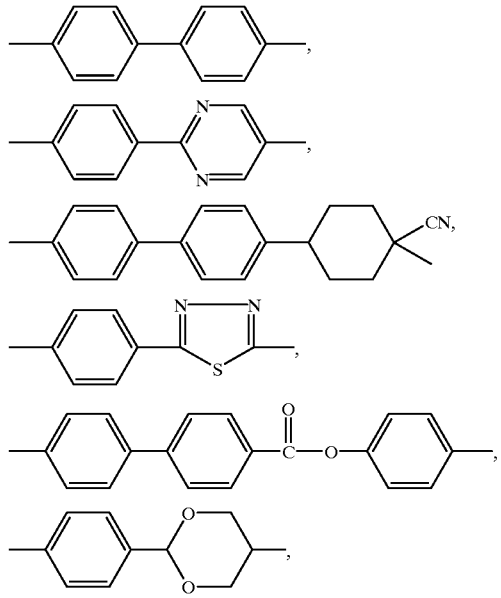

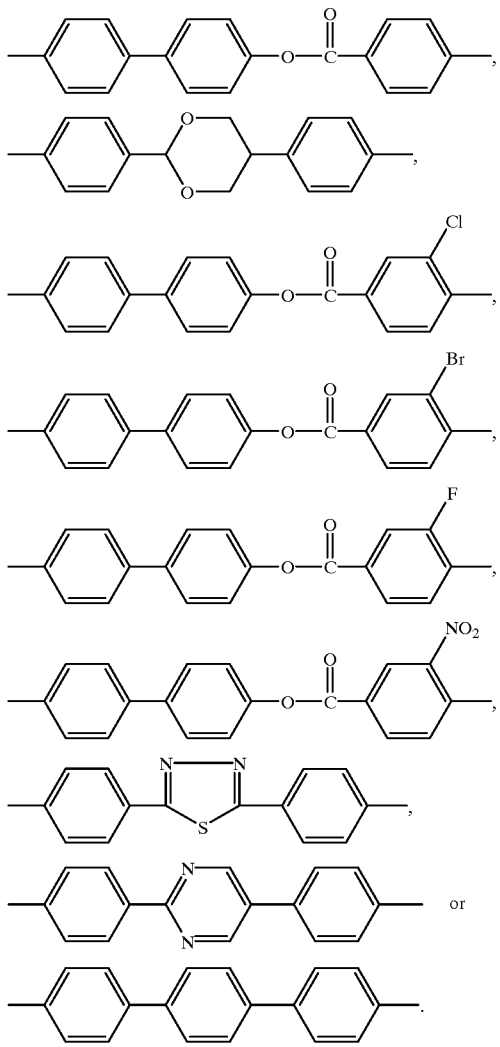

Particular preference is given to mesogenic groups M of the following formulae

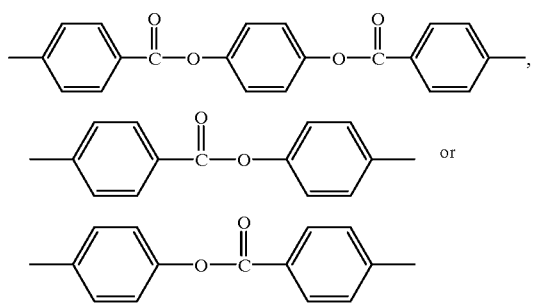

where each ring can carry up to three identical or different substituents from the following group:

$C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbonyloxy, $C_1$–$C_{20}$-alkylcarbonylamino, formyl, halogen, cyano, hydroxyl or nitro.

Besides fluorine, chlorine, bromine, cyano, formyl and hydroxyl, preferred substituents for the aromatic rings are in particular short-chain aliphatic radicals, such as methyl, ethyl, n-propyl, isopropyl, n-butyl, isobutyl, tert-butyl and alkoxy, alkoxy-carbonyl, alkylcarbonyl, alkylcarbonyloxy, alkylcarbonylamino and monoalkylaminocarbonyl radicals containing these alkyl groups.

The outer benzene rings in the particularly preferred groups M preferably have the following substitution patterns:

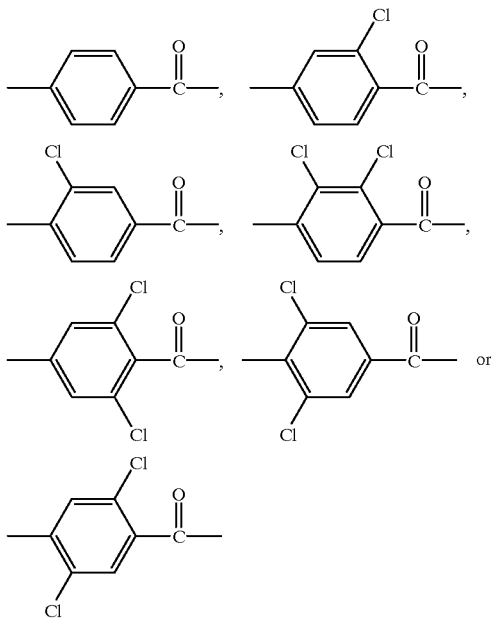

or are substituted analogously by F, Br, $CH_3$, $OCH_3$, CHO, $COCH_3$, $OCOCH_3$ or CN instead of Cl, it also being possible for the substituents to be mixed. Mention should also be made of the structures

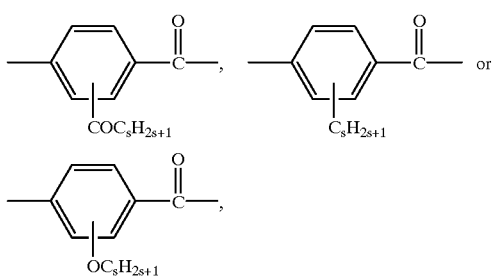

where s is from 2 to 20, preferably from 8 to 15.

The preferred substitution patterns of the central benzene ring in the particularly preferred groups M are the following:

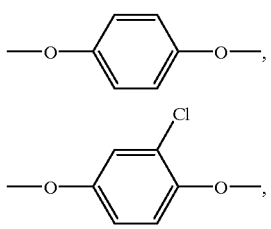

-continued
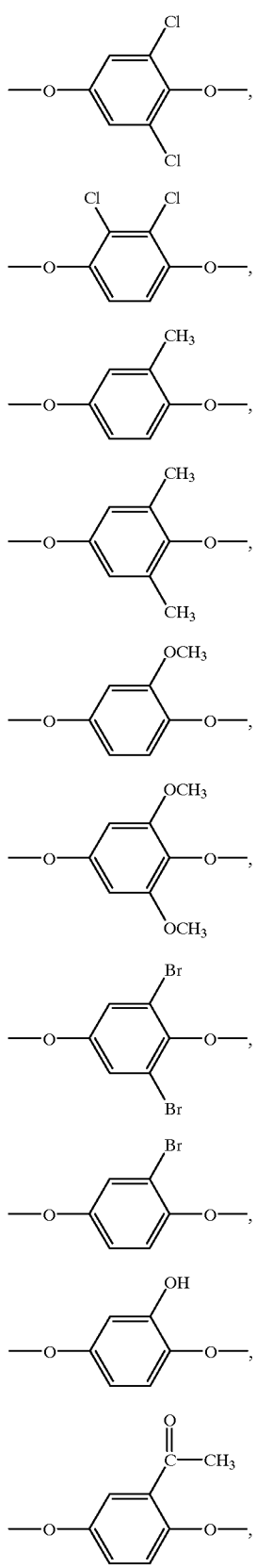
-continued
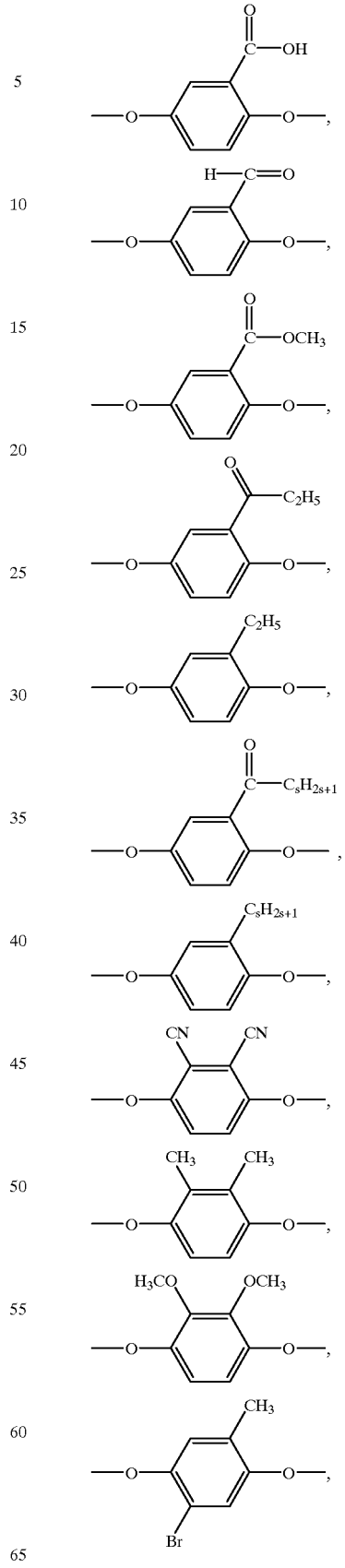

-continued

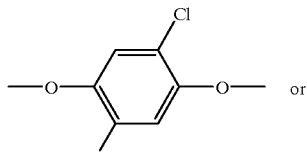 or

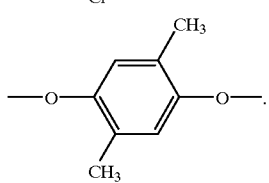.

Preferred novel compounds I are also those in which the radical pairs $Z^1$ and $z^2$, $Y^1$ and $Y^2$, $Y^3$ and $Y^4$ and $A^1$ and $A^2$ are in each case identical.

For industrial applications, especially in the printing sector, it is often important to adjust to a required viscosity.

It is therefore also possible for this purpose to prepare mixtures of the novel compounds I. Such mixtures usually have a lower viscosity than the pure components of the mixture and generally have lower liquid-crystalline phase temperatures so that, in some cases, they are suitable for applications at room temperature.

The molecule fragments occurring in the mixtures of the novel compounds may be not only, for example, "trinuclear", and unsubstituted or ring-substituted mesogenic groups M of the formula

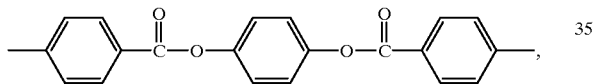

where in formula Ia
$Y^5$ is

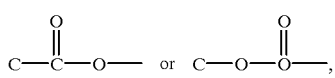

T is three identical radicals

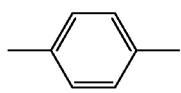

(for the unsubstituted case),
r is 2,
but also, for example, "binuclear ring" groups M of the formulae

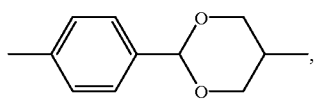

where in formula Ia
$Y^5$ is a single chemical bond,

T is different radicals

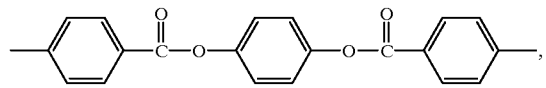

(unsaturated isocyclic) and

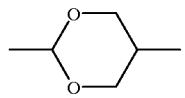

(saturated heterocyclic),
r is 1, or

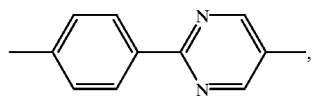

where in formula Ia
$Y^5$ is a single chemical bond,
T is different radicals

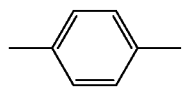

(unsaturated isocyclic) and

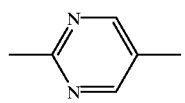

(unsaturated heterocyclic),
r is 1.

Particularly preferred "binuclear" mesogenic groups M in this connection are the fragments

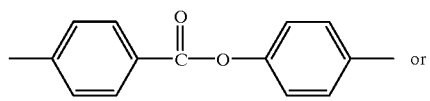 or

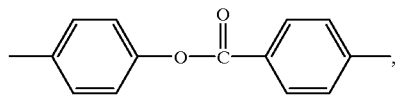, which may additionally be substituted on the aromatic rings as described above.

Also claimed according to the invention are liquid-crystal compositions which, besides compounds I, may comprise one or more compounds of the formula II $$Z^3-Y^6-A^3-Y^7-M-Y^8-P^1 \qquad II,$$

where
$Z^3$ are radicals containing reactive groups via which polymerization can be effected,
$Y^6-Y^8$ are a single chemical bond, oxygen, sulfur, —O—CO—, —CO—O—, —O—CO—O—, —CO—

NR—, —NR—CO—, —O—CO—NR—, —NR—CO—O— or —NR—CO—NR—, where at least one of the groups $Y^7$ and $Y^8$ is —O—CO—O—, —O—CO—NR—, —NR—CO—O or —NR—CO—NR—, $A^3$ is a spacer having 2 to 30 carbon atoms in which the carbon chain may be interrupted by ether oxygen, thioether sulfur or by nonadjacent imino or $C_1$–$C_4$-alkylimino groups, $P^1$ are radicals selected from the group of hydrogen, $C_1$–$C_{30}$-alkyl, $C_1$–$C_{30}$-acyl, $C_3$–$C_8$-cycloalkyl unsubstituted or substituted by one to three $C_1$–$C_6$-alkyl and where the carbon chain of the alkyl, acyl and cycloalkyl radicals may be interrupted by ether oxygen, thioether sulfur or by nonadjacent imino or $C_1$–$C_4$-alkylimino groups.

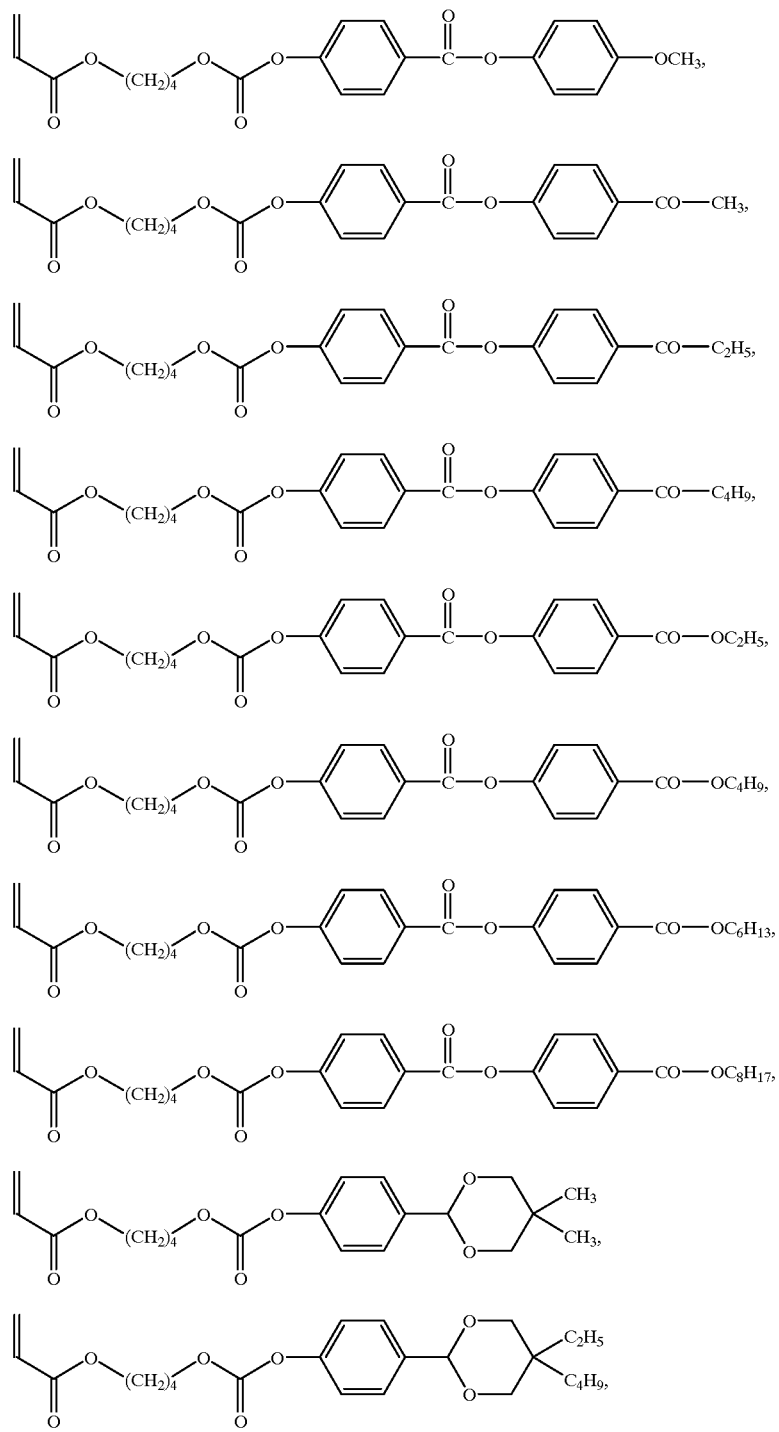

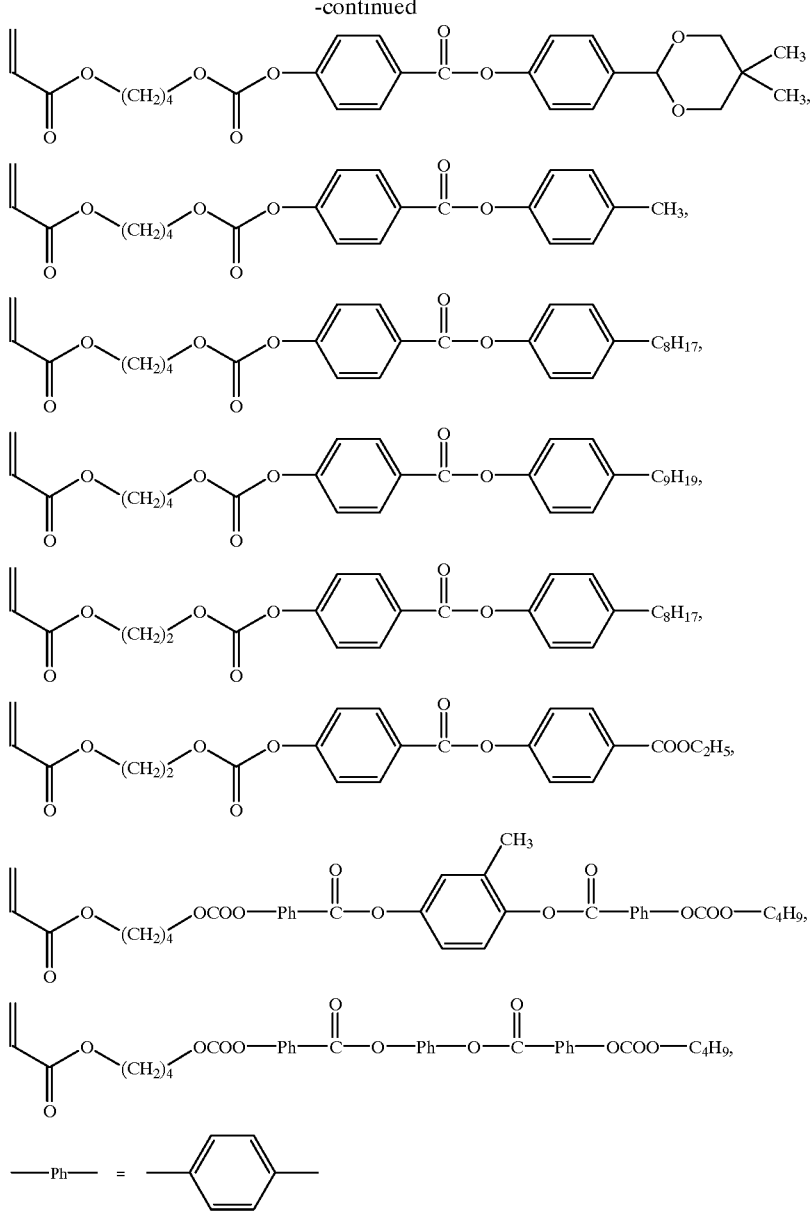

It is further possible to add one or more compounds of the formula III

P²—Y⁹—M—Y¹⁰—P³           III, where $P^2, P^3$ are radicals selected from the group of hydrogen, $C_1$–$C_{30}$-alkyl, $C_1$–$C_{30}$-acyl, $C_3$–$C_8$-cycloalkyl unsubstituted or substituted by one to three $C_1$–$C_6$-alkyl, and where the carbon chain of the alkyl, acyl and cycloalkyl radicals may be interrupted by ether oxygen, thioether sulfur or by nonadjacent imino or $C_1$–$C_4$-alkylimino groups, $Y^9, Y^{10}$ are a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups $Y^9$ and $Y^{10}$ is —O—CO—O—, —O—CO—NR—, —NR—CO—O or —NR—CO—NR—, M is a mesogenic group.

These would be, for example, compounds such as

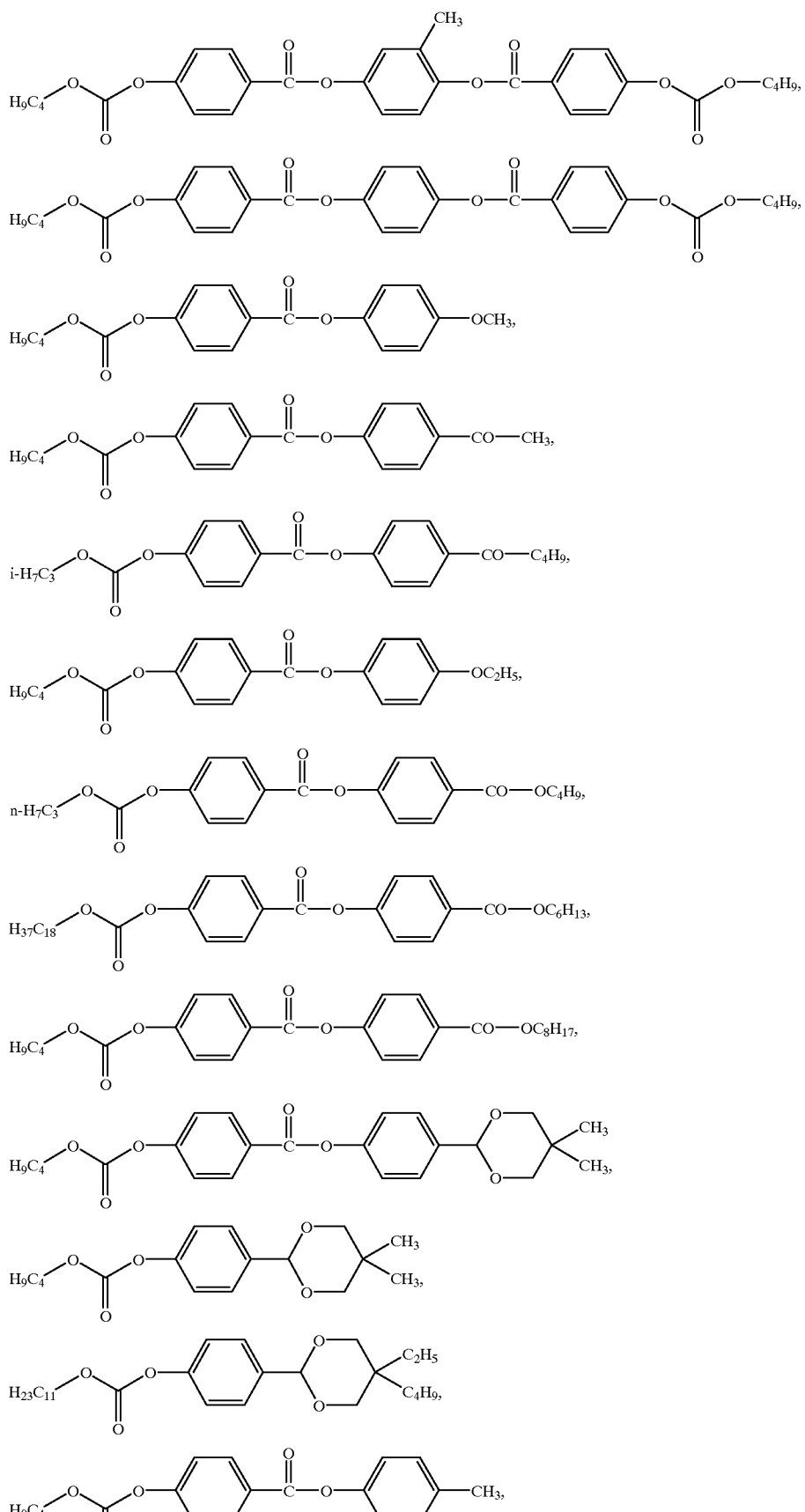

but also other compounds of the formula III, some of which are commercially available.

If the novel liquid-crystal compositions which, besides compounds of the formula I as components, also comprise compounds of the formulae II and III as components b) and c) respectively are polymerized, there is, owing to the addition of the latter two compounds, a reduction in the density of crosslinking of the resulting polymer. This makes it possible to adjust properties such as hardness, elasticity, glass transition temperature, permeability to liquids and gases etc. of the resulting polymerized products.

Liquid-crystal compositions which comprise one or more of compounds I, II and III may additionally comprise one or more chiral compounds. This results in cholesteric liquid-crystalline phases which have, in particular, interesting optical properties and, for example, reflect light of different wavelengths depending on the observation angle. Liquid-crystal compositions of this type are used, in particular, as cholesteric liquid-crystalline colorants.

Particularly suitable chiral components are those which, on the one hand, have a high twisting power and, on the other hand, are readily miscible with the liquid-crystalline compounds without adversely affecting the liquid-crystalline phase structure.

Examples of preferred chiral compounds are those of the formulae Ib, Ic, Id, Ie $$(Z^1-Y^5)_n X \qquad \text{Ib},$$

$$(Z^1-Y^1-A^1-Y^5)_n X \qquad \text{Ic},$$

$$(P^1-Y^5)_n X \quad \text{Id}$$

$$(Z^1-Y^1-A^1-Y^3-M-Y^4)_n X \qquad \text{Ie},$$

where the variables have the meanings stated for formulae I, Ia and II, n is a number from 1 to 6, and X is an n-valent chiral radical.

Examples of radicals X are:

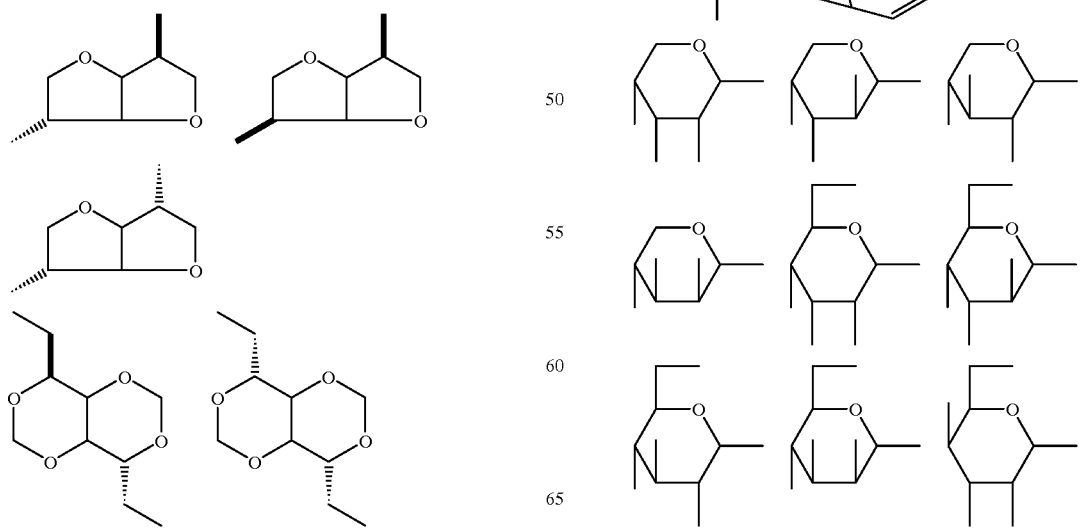

-continued
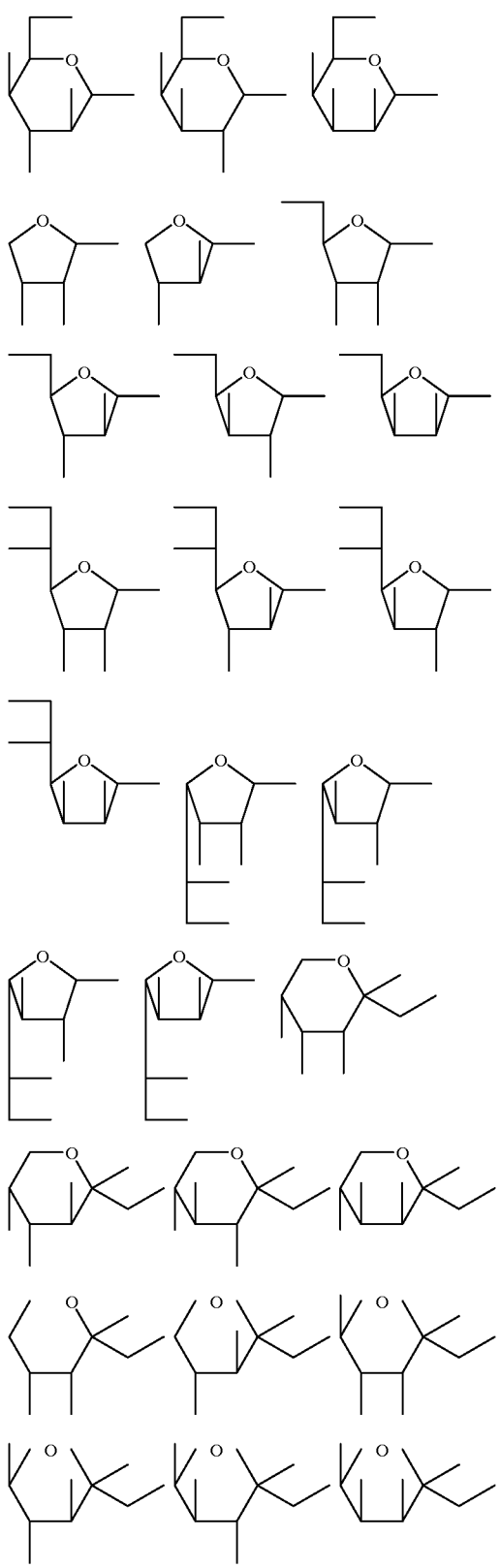
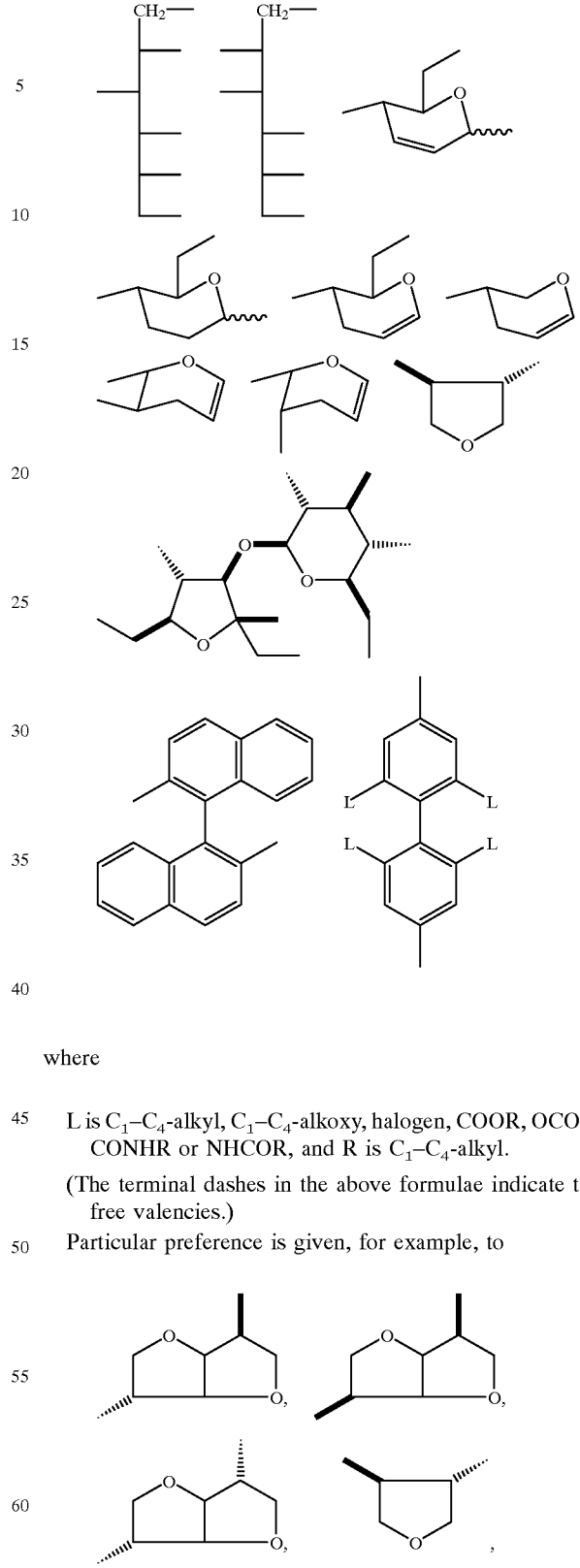
where
L is $C_1$–$C_4$-alkyl, $C_1$–$C_4$-alkoxy, halogen, COOR, OCOR, CONHR or NHCOR, and R is $C_1$–$C_4$-alkyl.
(The terminal dashes in the above formulae indicate the free valencies.)
Particular preference is given, for example, to
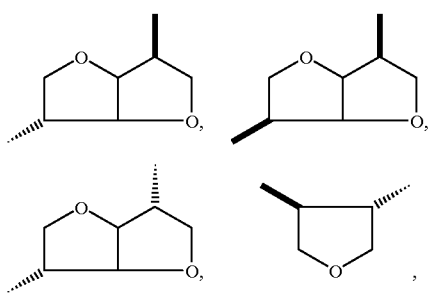

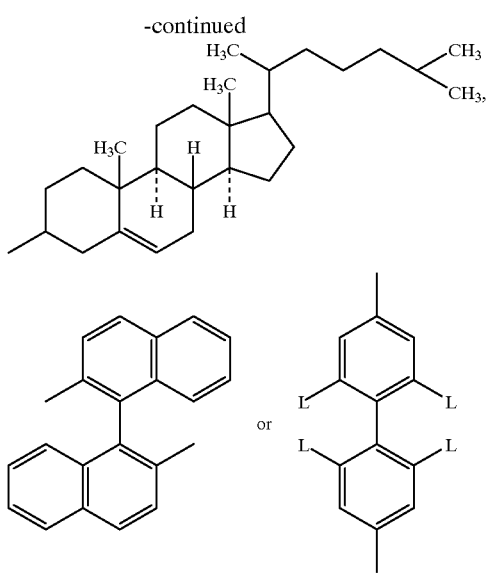

These and other preferred chiral components are mentioned, for example, in DE-A 43 42 280 and the earlier German Patent Applications 19520660.6 and 19520704.1.

Components a), b) and c) are preferably employed in the liquid-crystal compositions in molar proportions, based on the total amount of said components, of
a) 1–98 mol %,
b) 1–98 mol %,
c) 0.01–90 mol %,
where the total of the individual molar proportions must, of course, be 100 mol %.

If liquid-crystal compositions which, besides components a), b) and c), also contain one or more chiral compounds, are used it is preferred for the former components to be mixed in a proportion of from 60 to 99.999% by weight with the latter chiral compounds in a proportion of from 0.001 to 40% by weight, once again the proportions by weight being based on the total of the proportions of components a), b) and c) plus chiral compounds. The total of the proportions is, of course, once again 100% by weight.

Further novel liquid-crystal compositions contain 10–100% by weight, preferably 50–100% by weight, particularly preferably 60–100% by weight, of compounds I, I and II and/or III, in each case based on the total weight of the liquid-crystal composition. In addition, the mixtures may contain 0–90% by weight, preferably 0–50% by weight, of other monomers like the crosslinkers described hereinafter, and 0–50% by weight, preferably 0–10% by weight, of one or more polymerizable or nonpolymerizable chiral compounds.

It is possible by polymerizing the novel compounds or liquid-crystal compositions to fix the liquid-crystalline ordered state. The polymerization can take place, for example, thermally or photochemically depending on the polymerizable group. It is also possible to copolymerize other monomers with the novel compounds or liquid-crystal compositions. These monomers can be other polymerizable liquid-crystalline compounds, chiral compounds, which are likewise preferably copolymerized covalently, or conventional crosslinkers such as polyvalent acrylates, vinyl compounds or epoxides. In the particular case of isocyanates, isothiocyanates or epoxides as polymerizable liquid-crystalline compounds, the crosslinker is preferably a polyhydric alcohol so that, for example, urethanes can be formed. The amount of crosslinker must be matched to the polymerization conditions so that, on the one hand, satisfactory mechanical stability is achieved but, on the other hand, the liquid-crystalline phase behavior is not impaired. The amount of crosslinker therefore depends on the use of the polymers. For the preparation of pigments, a relatively large amount of crosslinker is advantageous, while the preparation of thermoplastic layers or, for example, for display alignment layers requires a relatively small amount of crosslinker. The amount of crosslinker can be determined by a few preliminary experiments.

A further modification of the polymerized products prepared from the novel compounds or liquid-crystal compositions is possible by adding polymeric auxiliaries before the polymerization. Auxiliaries of this type should preferably be soluble either in the initial mixtures or else in an organic solvent compatible with the initial mixtures. Typical representatives of such polymeric auxiliaries are, for example, polyesters, cellulose esters, polyurethanes and polyether- or polyester-modified or else unmodified silicones. The amount of polymeric auxiliary to be added where appropriate for the required purpose, its chemical nature and possibly also the amount and nature of a solvent are generally familiar to the skilled worker or can likewise be determined by a few preliminary experiments.

Besides the compounds of the formulae II (component b) and III (component c), it is also possible to admix with the polymerizable liquid-crysalline compounds of the formula I (component a) other compounds which are incorporated noncovalently into the polymeric network. Possible examples of these are commercially obtainable nematic liquid crystals.

Further additives may also be pigments, dyes and fillers.

With regard to pigments, these can be inorganic compounds such as iron oxides, titanium oxide and carbon black, organic compounds, for example pigments or dyes from the classes of monoazo pigments, monoazo dyes and their metal salts, disazo pigments, condensed disazo pigments, isoindoline derivatives, derivatives of naphthalene- or perylenetetracarboxylic acid, anthraquinone pigments, thioindigo derivatives, azomethine derivatives, quinacridones, dioxazines, pyrazoloquinazolones, phthalocyanine pigments or basic dyes such as triarylmethane dyes and their salts.

Further suitable pigments are those which confer an effect, such as aluminum or mica flakes or else pigments such as the pearlescent and effect pigments commercially obtainable under the names Iriodin® and Paliocrom®.

It is furthermore possible to add conventional fillers such as chalk, talc, gipsum, barytes, etc.

The novel compounds are prepared by methods known per se. In general, the moieties $Z^1$, $Z^2$, $A^1$, $A^2$ and M are linked to one another by condensation reactions in such a way that the bridges $Y^1$ to $Y^4$ are formed. The starting components here are selected so that the corresponding esters or amides are formed. This reaction principle also applies to the synthesis of the mesogenic group from the corresponding ring system components. The carbonate group is preferably formed by successive reaction of hydroxyl-carrying moieties with phosgene. Carbamate groups and urea groups are formed correspondingly from phosgene and amino compounds.

A preferred synthetic route for compounds of the formula I where the variables $Y^3$ and $Y^4$ are both —O—CO—O starts with reaction of a $Z^1$—CO—Cl acid chloride with a spacer diol with formation of an ester group as $Y^1$:

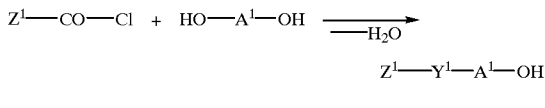

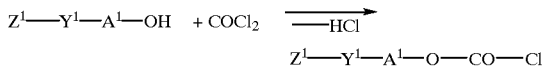

The resulting hydroxyl compound can then be reacted with a compound Cl—OC—M—CO—Cl or, preferably, first with one equivalent of phosgene in accordance with the following reaction

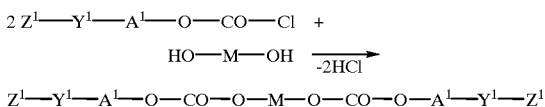

to form the corresponding chloroformate, and subsequently with a mesogen diol to give the target compound:

$$2\ Z^1\text{—}Y^1\text{—}A^1\text{—}O\text{—}CO\text{—}Cl\ +$$
$$HO\text{—}M\text{—}OH \xrightarrow{-2HCl}$$
$$Z^1\text{—}Y^1\text{—}A^1\text{—}O\text{—}CO\text{—}O\text{—}M\text{—}O\text{—}CO\text{—}O\text{—}A^1\text{—}Y^1\text{—}Z^1$$

In this case, a symmetrical compound in which $Z^1$—$Y^1$—$A^1$—$Y^3$— is identical to —$Y^4$—$A^2$—$Y^2$—$Z^2$ is formed. It is also possible in such a one-step reaction to react several different chloroformates as mixture or spatially separate, successively or simultaneously, with the mesogen diol or a mixture of mesogen diols. However, this results in mixtures of symmetrical and asymmetrical liquid-crystalline compounds. Asymmetrical compounds can be obtained deliberately by stepwise reaction with one equivalent of the mesogen diol followed by reaction with a compound Cl—CO—O—$A^2$—$Y^2$—$Z^2$.

The procedure for this is advantageously to deviate from the stoichiometric molar ratio of 1:2 for mesogen diol: ($Z^1$—$Y^1$—$A^1$—O—CO—Cl+$Z^2$—$Y^2$—$A^2$—O—CO—Cl) and to introduce the diol in a molar excess of from 5:2 to 20:2, preferably 10:2, in a solvent. The chloroformate $Z^1$—$Y^1$—$A^1$—O—CO—Cl is added, and the excess, unreacted mesogen diol is precipitated with a precipitant. After the solid has been filtered off, in a second step the chloroformate $Z^2$—$Y^2$—$A^2$—O—CO—Cl is added to the filtrate which contains the intermediate $Z^1$—$Y^1$—$A^1$—O—CO—O—M—OH which is readily soluble in both the solvent and the precipitant. A conventional workup results in the pure mixed compound $Z^1$—$Y^1$—$A^1$—$Y^3$—M—$Y^4$—$A^2$—$Y^2$—$Z^2$ or, in the case of an asymmetrical mesogenic group M or on use of a plurality of mesogen diols, a corresponding mixture of isomers or a mixture of asymmetrical compounds I.

Examples of solvents which can generally be employed for this are dimethylacetamide, N-methylpyrrolidone, dimethylformamide, methyl ethyl ketone or acetone, and of precipitants are methanol, ethyl acetate, dichloromethane or butyl acetate, the action as solvent or precipitant being, of course, dependent on the dissolving properties of the mesogen diols and, moreover, it being necessary for the intermediate to be readily soluble in the mixture of solvent and precipitant. For the example of the mesogen diol 1,4-bis(4-hydroxybenzoyloxy)-2-methylbenzene

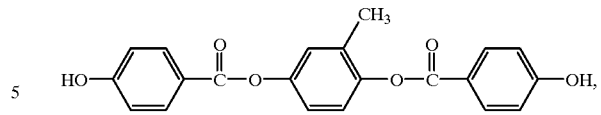

the combination of dimethylformamide and ethyl acetate as solvent and precipitant, respectively, is very suitable.

It is further advantageous, for trapping of the HCl produced, to add a base in an amount which is at least equimolar to the amount of chloroformate before each chloroformate addition step. Suitable for this purpose are tertiary amines such as trimethyl-, triethyl- or else N,N-dimethylcyclohexylamine, pyridine or else inorganic bases such as alkali metal or alkaline earth metal carbonates or bicarbonates, and mixtures of organic and inorganic bases.

Further bases which can be employed are alkali metal or alkaline earth metal acetates. It is preferred to add N,N-dimethylcyclohexylamine and potassium carbonate, either alone or in a mixture.

The reactions are generally carried out at from 0° C. to 60° C., usually from 40° C. to 50° C. The reactions last from 3 to 24 hours, depending on the reactivity of the reactants.

The workup usually involves diluting the reaction mixture with water and an organic extractant which is immiscible or of only low miscibility with water, and washing the organic phase several times with water and finally with aqueous mineral acid.

The organic extractant is removed by distillation under reduced pressure at from 20° C. to 40° C. To prevent premature polymerization of the product(s), conventional inhibitors such as methoxyphenol, Kerobit® BHT or phenothiazine, usually in a mixture, in amounts of from 0.01 to 1% by weight, based on the product(s), are added before the distillation. The mixture of inhibitors differing in volatility ensures adequate stabilization of the product(s) in both the liquid and vapor phases.

Preferably used as organic extractants are toluene or ethyl acetate. Concentrated hydrochloric acid is preferably used for the acid wash.

It is possible and preferred also to add diluents for the reaction of the mesogen diols with the chloroformates. These reduce the viscosity of the reaction mixture and thus ensure faster mixing of the reactants and thus a shortening of the reaction time. Examples of advantageous diluents which can be used are toluene, xylene, ethyl acetate, butyl acetate or else tetrahydrofuran or the various isomeric dioxanes. It is furthermore possible for the diluent itself to act as base, for example the abovementioned tertiary amines or else pyridine.

The novel preparation of the compounds of the formula II where the variables $Y^7$ and $Y^8$ are —O—CO—O— takes place in a similar way to the specific stepwise preparation of the mixed compounds $Z^1$—$Y^1$—$A^1$—O—CO—O—M—O—CO—O—$A^2$—$Y^2$—$Z^2$. In this case, either the mesogen diol can be reacted in the first step with the chloroformate $Z^3$—$Y^6$—$A^3$—O—CO—Cl and in the second step with $P^1$—O—CO—Cl, or the chloroformates are added in the reverse sequence.

If it is intended to prepare a liquid-crystal composition which, besides compound I, also comprises compounds II and III, it can be prepared primarily by mixing the individual compounds in the abovementioned preferred proportions.

A simple way consists of reacting one or more diols with one or more chloroformates of the formula $Z^1$—$Y^1$—$A^1$—O—CO—Cl and with one or more chloroformates of the formula $P^1$—O—CO—Cl. In this case, the chloroformates are added either simultaneously but separately or in the form of a mixture. If particular compounds I, II and III are to be prepared specifically in above or below the stoichiometric amount, it is also expedient to add the various chloroformates stepwise.

The preferred molar ratio of chloroformate(s) $Z^1$—$Y^1$—$A^1$—O—CO—Cl to chloroformate(s) $P^1$—O—CO—Cl for preparing such liquid-crystal compositions is from 99:1 to 20:80, preferably from 99:1 to 40:60. A ratio of 50:50 is particularly preferably chosen.

If mixtures of chloroformates are employed, and if the reactivities of the chloroformates are identical, both with one another and toward the diol HO—M—OH or the corresponding monohydroxy intermediate (singly substituted mesogen diol), it is possible to determine the (random) distribution of the compounds I, II and III in accordance with the statements below. For simplicity, the following definitions are given now:

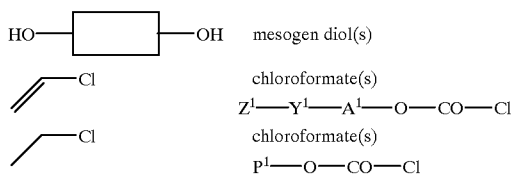

Reaction of the diol(s) with a mixture of chloroformates in the molar ratio of

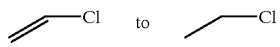

of 99:1 results, in the ideal case, in the following distribution after the first substitution

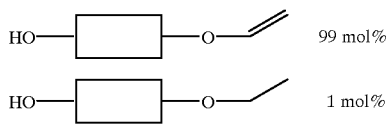

Each of these intermediates in turn undergoes second substitution in the above ratio of 99:1, ie.

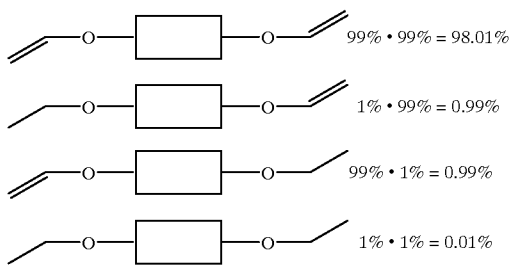

If the two products with mixed substituents are identical, ie. if the mesogen diol is symmetrical, the resulting ratio of compounds I to II to III is 98.01%:1.98% (=2×0.99%):0.01%.

Similarly, for a corresponding chloroformate mixture in the molar ratio 20:80 or 40:60 or 50:50, the resulting molar ratio of compounds I, II and III is 4%:32% (=2×16%):64% or 16:48% (=2×24%):36% or 25%:50% (=2×25%):25%.

It is possible to form the various other groups $Y^1$–$Y^4$ in a similar way, preferably reacting acid halides with the appropriate amino or hydroxyl compounds. Oxygen and sulfur bridges are introduced into the compounds in a known manner by ether synthesis methods.

Further details of the preparations of the compounds are given in WO 95/22586, WO 95/24454 and WO 95/24455.

The novel liquid-crystal compositions are outstandingly suitable for coating surfaces. A process for the production of such coatings having a liquid-crystalline ordered state comprises diluting the novel liquid-crystal compositions, which may comprise further polymerizable compounds and chiral compounds, if desired with a diluent to reduce the viscosity, applying the mixture to a substrate, effecting a liquid-crystalline alignment and then polymerizing the compounds applied to the substrate.

The liquid-crystalline alignment is formed either spontaneously during application or is achieved by known physical methods, for example rubbing or application of an electric or magnetic field.

If, for example, it is intended to use the novel liquid-crystal composition in the screen printing sector, the viscosity thereof can be reduced not only by said addition of diluents or by using mixtures of novel compounds I and II but also through the proportions of noncrosslinking compound III. By contrast with this, higher viscosities can be tolerated or are even desired for example in the automotive paints sector.

The novel compounds or liquid-crystal compositions are used, for example, for producing optical display devices, in particular for producing alignment layers in liquid-crystal displays. The compounds or compositions can also be used as polymerizable matrix components for polymer-dispersed displays.

Further possible uses are photocrosslinkable adhesives based on liquid crystals.

The novel compounds or liquid-crystal compositions are particularly preferably used in cholesteric liquid-crystalline mixtures which are used as liquid-crystalline colorants. Particular mention should be made in this context of automotive paints based on cholesteric liquid-crystal systems. These paints can either be produced by direct coating of the substrates or may contain pigments which comprise the novel compounds in a cholesteric liquid-crystalline ordered state fixed by polymerization.

The novel liquid-crystal compositions can also be used to produce pigments. This involves polymerization of the liquid-crystal composition and comminuting and grading the resulting polymer using conventional units. This preferably involves the initial composition being applied as a thin layer with a knife and, if desired, being additionally aligned in an electric or magnetic field. Pigments in platelet form are also obtainable in this way.

EXAMPLES

| Explanation of symbols: | | | |
|---|---|---|---|
| n.d. | not determined | cr | crystalline |
| s | smectic | i | isotropic |
| n | nematic | ch | cholesteric |

The following notation is used to characterize the phase behavior:

Example a): cr 78–83 n 87–88 i means that the crystalline phase (cr) is coexistent with the nematic phase (n) at from 78 to 83° C. The range of coexistence of nematic and isotropic phase (i) is from 87 to 88° C. Above 88° C. an isotropic "clarified" melt exists.

Example b): cr 77 i means that the transition from the crystalline phase (cr) to an isotropic phase (i) = melt takes place at 77° C.

The phase behavior of the compounds or mixtures was investigated by polarized-light microscopy. The temperature was controlled by means of a Mettler FP 80/82 type heated stage.

Viscosities were determined with a Rheometrics dynamic spectrometer (supplied by Rheometrics) with cone/plate geometry.

Coatings were prepared from some mixtures using a flat knife and were assessed either visually or by means of a spectrometer (Hitachi U-2000 supplied by Hitachi). On visual assessment, the meaning of, for example, "red-green" is that the coating showed a red color when viewed perpendicularly and showed a green color hen viewed at a small angle. The measured wavelengths $\lambda(\perp)$ relate to the reflected light viewed perpendicularly.

Preparations
Preparation Method 1
Preparation of the compounds (Examples 1 to 14)

TABLE 1

| Ex. | $R^1$ | $R^2$ | n | Liquid-crystalline temperature range [° C.] |
|---|---|---|---|---|
| 1 | H | H | 2 | 124–162 |
| 2 | H | H | 4 | 71–>100 (polymerized) |
| 3 | H | H | 6 | n.d. |
| 4 | H | H | 8 | 69–136 |
| 5 | $CH_3$ | H | 2 | 117–166 |
| 6 | $CH_3$ | H | 4 | 58–119 |
| 7 | $CH_3$ | H | 6 | 53–110 |
| 8 | $CH_3$ | H | 8 | 46–80 |
| 9 | Cl | H | 2 | 80–120 |
| 10 | Cl | H | 4 | <20–95 |
| 11 | Cl | H | 6 | <20–51 |
| 12 | Cl | H | 8 | 45–100 |
| 13 | H | $CH_3$ | 2 | 155–169 |
| 14 | H | $CH_3$ | 4 | 103–>130 (polymerized) |

Preparation Method 2

As) Preparation of the compound (Example 15)

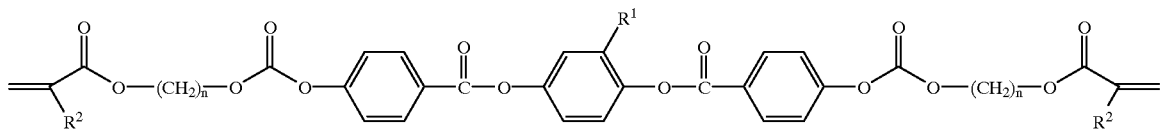

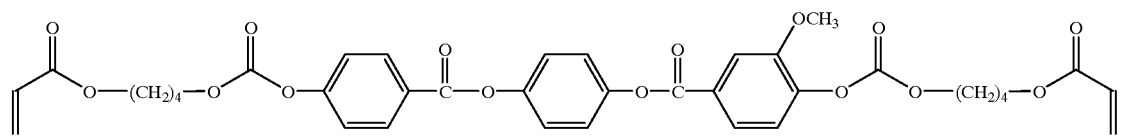

A solution of 12 mmol of a chloroformate

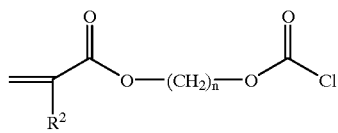

in 5 ml of dichloromethane was added dropwise to a solution of 5 mmol of 1,4-bis(4-hydroxybenzoyloxy)-2-$R^1$-benzene (mesogen diol) 20 ml of pyridine at 0° C., after which the reaction mixture was stirred at room temperature for 3 hours. Dilute hydrochloric acid was then added, whereupon the product precipitated as a solid, and it was filtered off, washed and purified by recrystallization.

The details of these experiments and the results thereof are to be found in Table 1 below.

95.1 g (0.25 mol) of 1-(3-methoxy-4-hydroxybenzoyloxy)-4-(4-hydroxybenzoyloxy)benzene were dissolved in 182 ml of dimethylformamide and 95.25 g (0.75 mol) of dimethylcyclohexylamine and, at room temperature, 124.96 g (0.605 mol) of acryloyloxybutyl chloroformate were added dropwise over the course of 30 minutes. The mixture was then stirred at 40° C. for 3.5 h and at room temperature overnight. Addition of water was followed by dilution with ethyl acetate, adjustment to pH 1 with concentrated hydrochloric acid, removal of the aqueous phase and washing of the organic phase with water twice. After the organic phase had been dried, the ethyl acetate was removed under reduced pressure, and the crude product was purified by filtration through silica gel with the eluent petroleum ether/ethyl acetate 2:1. The product showed the following phase behavior:

cr 78–83 n 87–88 i

Ab) Preparation of the compound (Example 16)

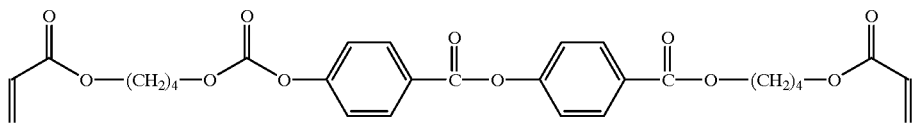

96.1 g (0.25 mol) of the compound

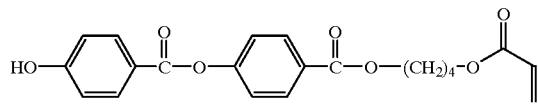

were dissolved in 182 ml of dimethylformamide and 47.6 g (0.375 mol) of dimethylcyclohexylamine and, at room temperature, 62.5 g (0.303 mol) of acryloyloxybutyl chloroformate were added dropwise over the course of 30 minutes. The mixture was then stirred at 40° C. for 3.5 h and at room temperature overnight. Addition of water was followed by dilution with ethyl acetate, adjustment to pH 1 with concentrated hydrochloric acid, removal of the aqueous phase and washing of the organic phase with water twice. After the organic phase had been dried, the ethyl acetate was removed under reduced pressure, and the crude product was purified by filtration through silica gel with the eluent petroleum ether/ethyl acetate 2:1. A pure product was obtained as oil.

Ac) Preparation of the compounds (Examples 17 to 22)

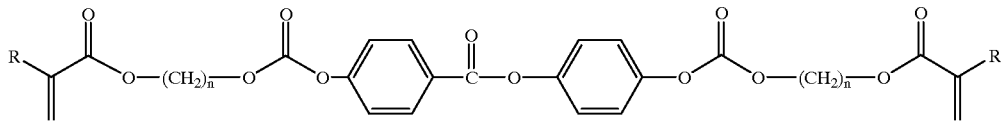

57.5 g (0.25 mol) of 4-(4-hydroxybenzoyloxy)phenol were dissolved in 182 ml of dimethylformamide and 95.25 g (0.75 mol) of dimethylcyclohexylamine and, at room temperature, 0.605 mol of the chloroformate

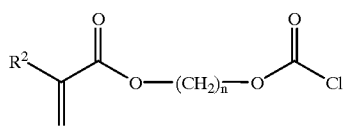

was added dropwise over the course of 30 minutes. The mixture was then stirred at 40° C. for 3.5 h and at room temperature overnight. Addition of water was followed by dilution with ethyl acetate, adjustment to pH 1 with concentrated hydrochloric acid, removal of the aqueous phase and washing of the organic phase with water twice. After the organic phase had been dried, the ethyl acetate was removed under reduced pressure, and the crude product was purified by filtration through silica gel with the eluent petroleum ether/ethyl acetate 2:1.

The details of the experiments are to be found in Table 2 below.

TABLE 2

| Ex. | R | n | Phase behavior |
|---|---|---|---|
| 17 | H | 2 | n.d. |
| 18 | H | 4 | cr 41 i |
| 19 | H | 6 | n.d. |
| 20 | $CH_3$ | 2 | n.d. |
| 21 | $CH_3$ | 4 | n.d. |
| 22 | $CH_3$ | 6 | n.d. |

Ba) Preparation of the compounds (Examples 23 to 27)

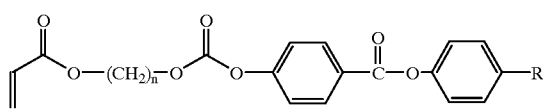

0.25 mol of the compound

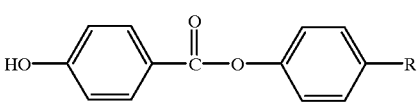

was dissolved in 182 ml of dimethylformamide and 47.6 g (0.375 mol) of dimethylcyclohexylamine and, at room temperature, 0.303 mol of the chloroformate

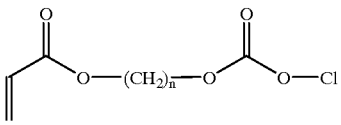

was added dropwise over the course of 30 minutes. The mixture was then stirred at 40° C. for 3.5 h and at room temperature overnight. Addition of water was followed by dilution with ethyl acetate, adjustment to pH 1 with concentrated hydrochloric acid, removal of the aqueous phase and washing of the organic phase with water twice. After the organic phase had been dried, the ethyl acetate was removed under reduced pressure, and the crude product was purified by filtration through silica gel with the eluent petroleum ether/ethyl acetate 2:1.

The details of the experiments are to be found in Table 3 below.

TABLE 3

| Ex. | R | n | Phase behavior |
|---|---|---|---|
| 23 | $OCH_3$ | 4 | cr 51 i |
| 24 | $CH_3$ | 4 | cr 39 i |
| 25 | $C_8H_{17}$ | 2 | oil |
| 26 | $C_8H_{17}$ | 4 | oil |
| 27 | $C_9H_{19}$ | 4 | oil |
| 28 | $COCH_3$ | 4 | cr 77 i |
| 29 | $COC_2H_5$ | 4 | cr 59 n 68 i |
| 30 | $COC_4H_9$ | 4 | cr 50–52 n 58–59 i |
| 31 | $COOC_2H_5$ | 2 | n.d. |
| 32 | $COOC_2H_5$ | 4 | cr 48 i |
| 33 | $COOC_4H_9$ | 4 | cr 30–32 i |
| 34 | $COOC_6H_{13}$ | 4 | cr 39–40 i |
| 35 | $COOC_8H_{17}$ | 4 | cr 38–40 i |
| 36 | 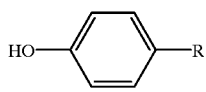 | 4 | cr 86 i |
| 37 | | 4 | cr 60–62 i |

TABLE 4

| Ex. | R | Phase behavior |
|---|---|---|
| 38 | $OCH_3$ | oil |
| 39 | | oil |
| 40 | | oil |

Preparation Method 3

Preparation of the compound (Example 6)

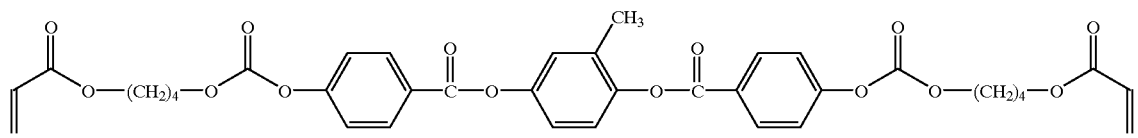

Bb) Preparation of the compounds (Examples 38 to 40)

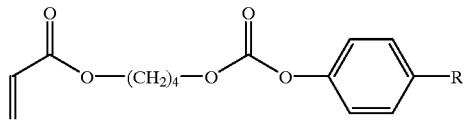

0.25 mol of the compound

HO—⟨ ⟩—R was dissolved in 182 ml of dimethylformamide and 47.6 g (0.375 mol) of dimethylcyclohexylamine and, at room temperature, 62.5 g (0.303 mol) of acryloyloxybutyl chloroformate were added dropwise over the course of 30 minutes. The mixture was then stirred at 40° C. for 3.5 h and at room temperature overnight. Addition of water was followed by dilution with ethyl acetate, adjustment to pH 1 with concentrated hydrochloric acid, removal of the aqueous phase and washing of the organic phase with water twice. After the organic phase had been dried, the ethyl acetate was removed under reduced pressure, and the crude product was purified by filtration through silica gel with the eluent petroleum ether/ethyl acetate 2:1.

The details of the experiments are to be found in Table 4 below.

364 g (1.0 mol) of 1,4-bis(4-hydroxybenzoyloxy)-2-methylbenzene and 303.5 g (2.2 mol) of potassium carbonate were suspended in 1 liter of N-methylpyrrolidone and, at room temperature, 495.6 g (2.4 mol) of acryloyloxybutyl chloroformate were added over the course of 30 minutes. The mixture was stirred at 40° C. for 30 minutes and then 151.0 g (1 mol) of dimethylcyclohexylamine were added, and the mixture was stirred at 40° C. for a further 3 h. Then 2 liters of toluene were added and the mixture was extracted by stirring twice with 2 liters of water each time. After the aqueous phase had drained off, 2 liters of water were added and the pH was adjusted to 1 with 128 g of concentrated hydrochloric acid. A further two extractions by 2 liters of water each time were then carried out. After removal of the aqueous phase, 85 mg of Kerobit BHT and 85 mg of methoxyphenol were added and the toluene was evaporated off under reduced pressure at a maximum bath temperature of 40° C. The crude yield was 730.6 g. Filtration through silica gel with petroleum ether/ethyl acetate as eluent resulted in 678.7 g (96%) of 1,4-bis(4-acryloyloxybutoxycarbonyloxybenzoyloxy)-2-methylbenzene (phase behavior: cr 58 n 122 i).

Preparation Method 4

A) Selective preparation of asymmetrical compounds (Examples 41 and 42)

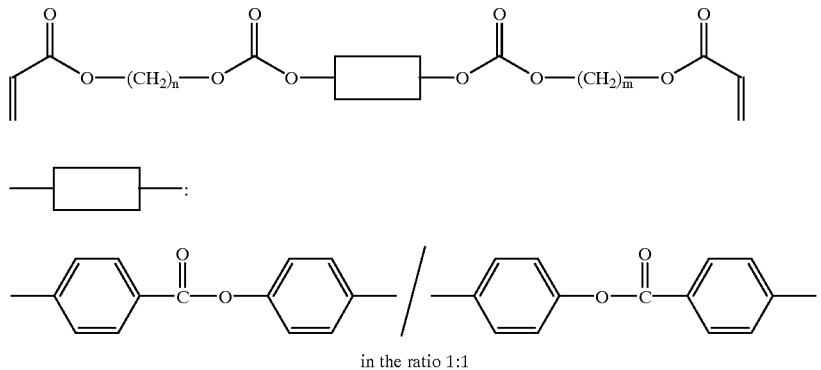

in the ratio 1:1

23 g (0.1 mol) of 4-(4-hydroxybenzoyloxy)phenol were dissolved in 100 g of dimethylformamide, and 1.2 g (0.01 mol) of dimethylcyclohexylamine were added. Then 0.01 mol of the chloroformate

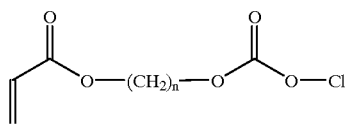

was added at room temperature. The mixture was stirred at 40° C. for 4 h and then 200 ml of ethyl acetate were added. The precipitated solid (excess 4-(4-hydroxybenzoyloxy) phenol) was filtered off with suction, and the filtrate was heated to 80° C. After about 180 ml of ethyl acetate had been distilled off, 0.01 mol of the chloroformate

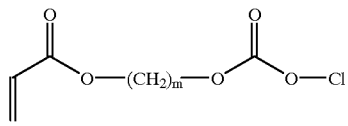

and a further 1.2 g (0.01 mol) of dimethylcyclohexylamine were added to the mother liquor, which was then stirred at 40° C. for 4 h. The reaction mixture was poured into 200 ml of water and extracted three times with 100 ml of ethyl acetate each time. The combined organic phases were dried over sodium sulfate and, after removal of the solvent, the crude product was purified by chromatography to result in a mixture of the two isomeric diacrylates

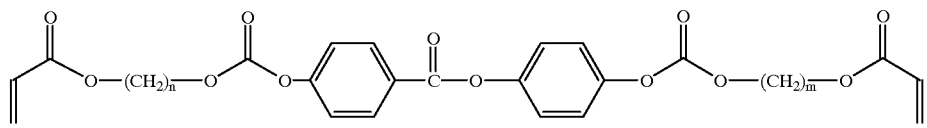

and

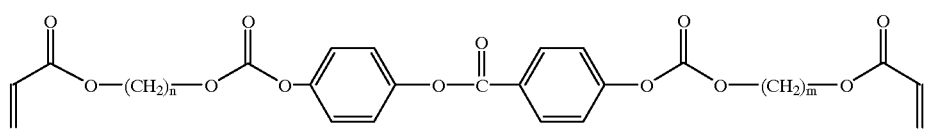

Table 5 contains details of the experiments.

TABLE 5

| Ex. | n | m | Phase behavior |
|---|---|---|---|
| 41 | 2 | 4 | n.d. |
| 42 | 4 | 6 | n.d. |

B) Selective preparation of the asymmetrical compound (Example 43)

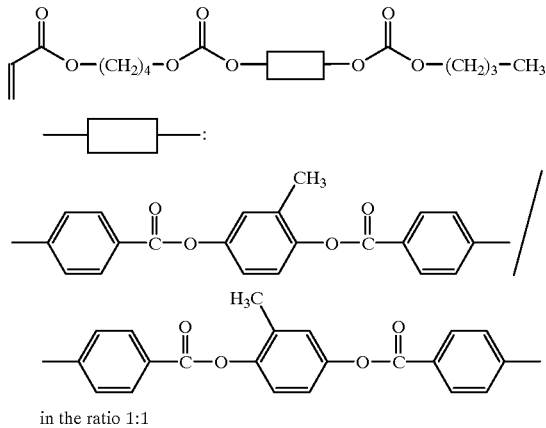

in the ratio 1:1

36.4 g (0.1 mol) of 1,4-bis(4-hydroxybenzoyloxy)-2-methylbenzene were dissolved in 100 g of dimethylformamide, and 1.2 g (0.01 mol) of dimethylcyclohexylamine were added. Then 2.08 g (0.01 mol) of acryloyloxybutyl chloroformate were added at 15 to 20° C. The mixture was stirred at 40° C. for 4 h and then 200 ml of ethyl acetate were added. The precipitated solid was filtered off with suction, and the filtrate was heated to 80° C. After about 180 ml of ethyl acetate had been distilled off, 1.36 g (0.01 mol) of butyl chloroformate and a further 1.2 g (0.01 mol) of dimethylcyclohexylamine were added to the mother liquor, which was then stirred at 40° C. for 4 h. The reaction mixture was poured into 200 ml of water and extracted three times with 100 ml of ethyl acetate each time. The combined organic phases were dried over sodium sulfate and, after removal of the solvent, the crude product was purified by chromatography to result in 5.72 g (90%) of the two isomeric monoacrylates yphenol and 126.8 mg of phenothiazine to the organic phase, the toluene was removed by distillation under reduced pressure at a bath temperature of 40° C.

The results of the experiments are compiled in Table 6 below.

TABLE 6

| Ex. | Molar ratio CF1*):CF2**) | Phase behavior |
| --- | --- | --- |
| 44 | 70:30 | s 47 n 127–131 i |
| 45 | 80:20 | s 54 n 145 i |
| 46 | 90:10 | s 56–57 n 155–156 i |

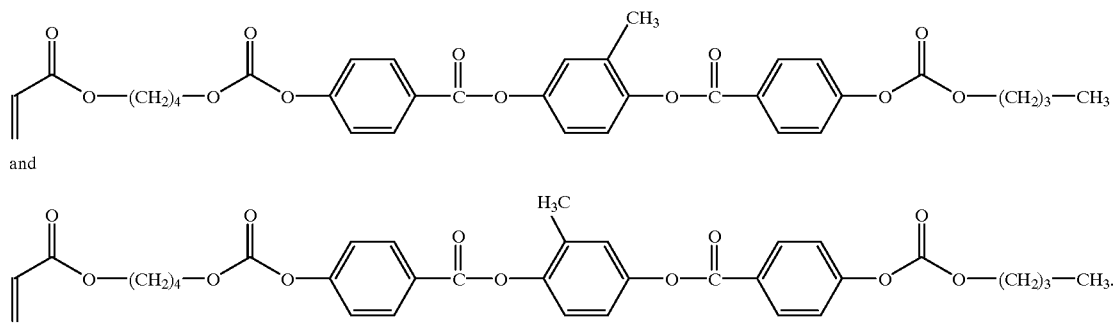

and

Phase Behavior: n 134 i
Preparation Method 5
Aa) Preparation of random mixtures of compounds (Examples 44 to 46)

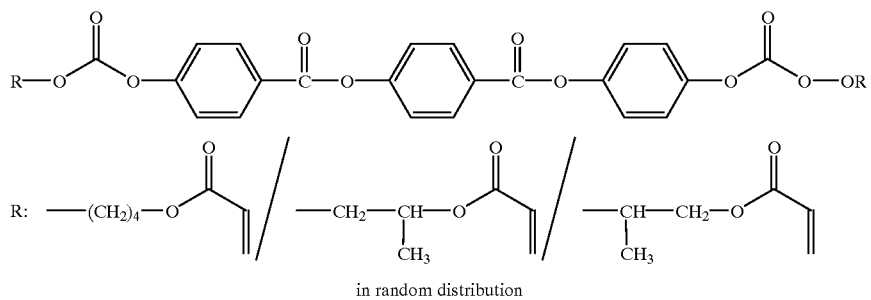

in random distribution 350 g (1.0 mol) of 1,4-bis(4-hydroxybenzoyloxy)benzene were introduced into 728 ml of dimethylformamide, and 381 g (3 mol) of dimethylcyclohexylamine were added. Between 0° C. and 5° C., a mixture of 2.1 mol of acryloyloxybutyl chloroformate (chloroformate CF1) and 2-acryloyloxy-2-methylethyl chloroformate/2-acryloyloxy-1-methylethyl chloroformate (chloroformate CF2; a mixture of the two isomeric compounds results from the preparation of the chloroformate, but the relative proportions of the 2- and 1-methyl compounds could not be determined) in the molar ratio of the butyl compound to the mixture of the isomeric methyl ethyl compounds of 70:30 or 80:20 or 90:10 was added dropwise over the course of 30 minutes. The reaction mixture was then stirred at 40° C. for 3 h.

The mixture was diluted with 2 liters of toluene and 1 liter of water and acidified with 120 ml of concentrated hydrochloric acid. Draining off the aqueous phase was followed by washing to neutrality with 2×500 ml of water. After addition of 63.5 mg of Kerobit® BHT, 63.5 mg of methox- TABLE 6-continued

| Ex. | Molar ratio CF1*):CF2**) | Phase behavior |
| --- | --- | --- |

*) CF1: 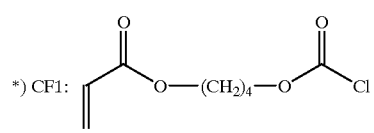

TABLE 6-continued

| Ex. | Molar ratio CF1*):CF2**) | Phase behavior |
|---|---|---|

**)  CF2: 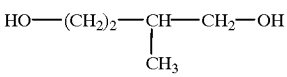

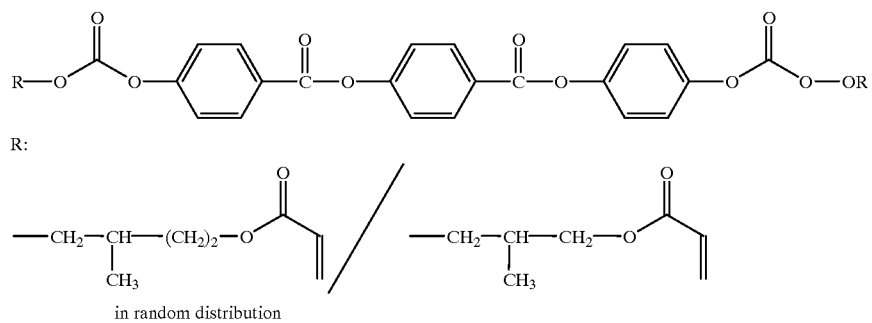

Ab) As in Aa), a random mixture of compounds (Example 47)

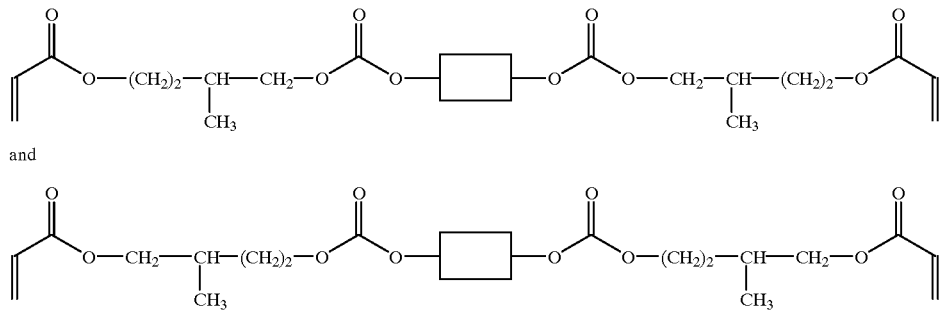

in random distribution was obtained by reacting 1.0 mol of 1,4-bis(4-hydroxybenzoyloxy)benzene with 2.1 mol of a 1:1 mixture of the chloroformate

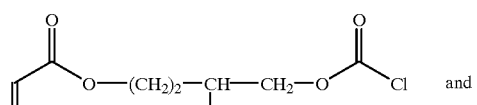 and

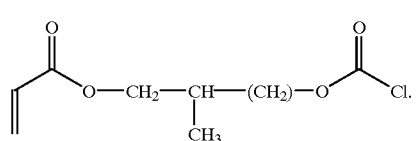

The mixture of chloroformates can be prepared by reacting the diol $$HO-(CH_2)_2-CH(CH_3)-CH_2-OH$$

with one equivalent each of acryloyl chloride and phosgene.

The resulting mixture of the abovementioned compounds was not analyzed, but the contents of the two symmetrical compounds and of the asymmetrical compound

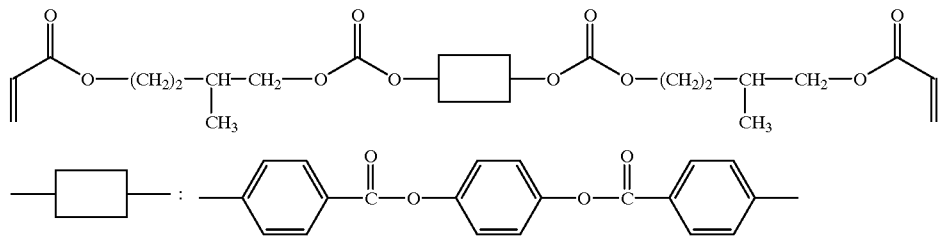

are expected to be in the molar ratio of (approximately) 25:25:50.

B) Preparation of random mixtures of compounds (Examples 48 and 49)

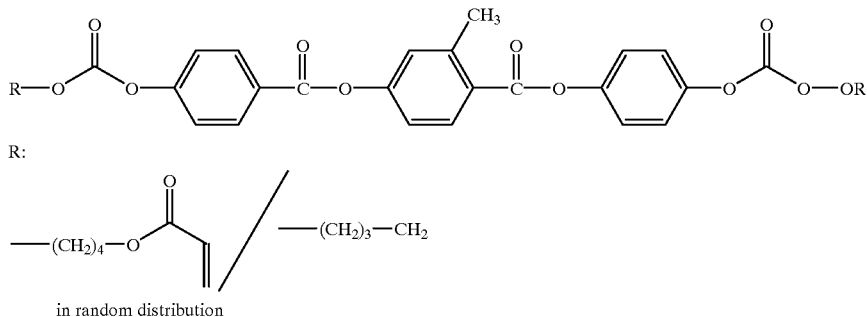

in random distribution 364 g (1.0 mol) of 1,4-bis(4-hydroxybenzoyloxy)benzene were introduced into 728 ml of dimethylformamide, and 381 g (3 mol) of dimethylcyclohexylamine were added. Between 0° C. and 5° C., a mixture of 2.1 mol of acryloyloxybutyl chloroformate (chloroformate CF1) and butyl chloroformate (chloroformate CF3) in the molar ratio of 50:50 or 90:10 was added dropwise over the course of 30 minutes. The reaction solution was then stirred at 40° C. for 3 h.

The mixture was diluted with 2 liters of toluene and 1 liter of water and acidified with 120 ml of concentrated hydrochloric acid. Draining off the aqueous phase was followed by washing to neutrality with 2×500 ml of water. After addition of 63.5 mg of Kerobit® BHT, 63.5 mg of methoxyphenol and 126.8 mg of phenothiazine to the organic phase, the toluene was removed by distillation under reduced pressure at a bath temperature of 40° C.

The results of the experiments are summarized in Table 7 below.

TABLE 7

| Ex. | Molar ratio CF1*):CF3**) | Phase behavior |
|---|---|---|
| 48 | 50:50 | cr 40–48 n 150–152 i |
| 49 | 90:10 | cr 38–48 n 109–113 i |

*) CF1: 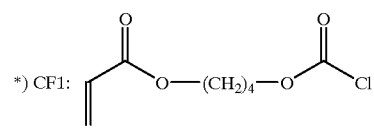

TABLE 7-continued

| Ex. | Molar ratio CF1*):CF3**) | Phase behavior |
|---|---|---|

**) CF3: 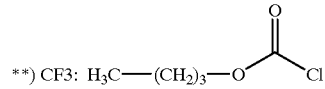

The mixtures of Examples 48 and 49 were analyzed by chromatography. This resulted in the mole percentages of the individual components of the mixtures which were listed in Table 8.

a) (corresponds to a novel compound of the formula I)

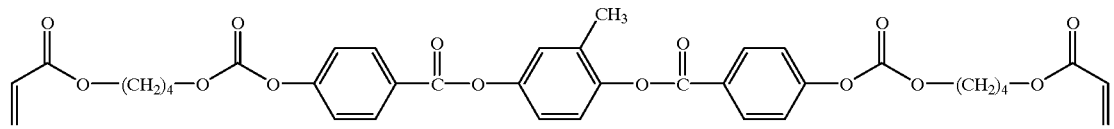

b) (corresponds to a novel compound of the formula II)

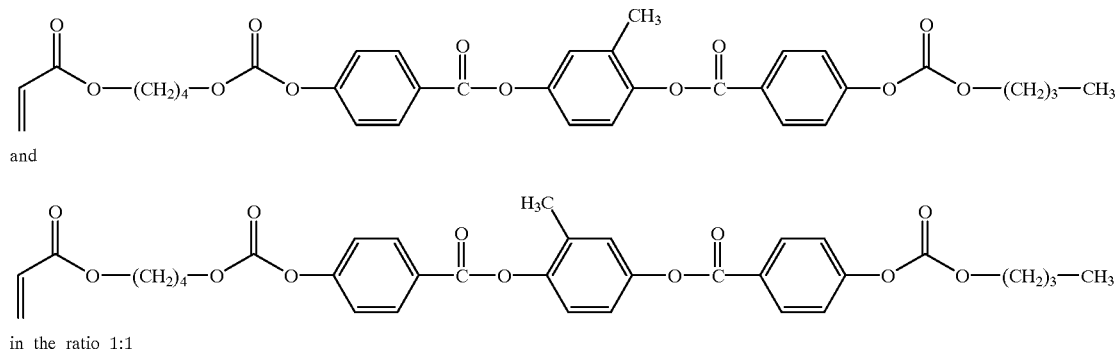

in the ratio 1:1 c) (corresponds to a compound of the formula III)

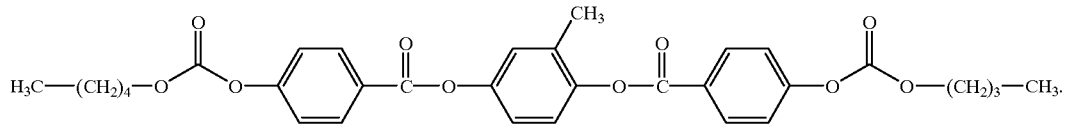

For comparison, Table 8 also lists the mole percentages calculated for components a, b and c which can be derived from the molar ratios of the chloroformates CF1 and CF3 employed.

TABLE 8

| Component (mol %) | | Example 48 | Example 49 |
|---|---|---|---|
| a | determined | 28 | 78 |
|   | calculated | 25 | 81 |
| b | determined | 48 | 20 |
|   | calculated | 50 (2 · 25) | 18 (2 · 9) |
| c | determined | 24 | 2 |
|   | calculated | 25 | 2 |

Mixtures:

The numbers in the following tables refer to percent by weight of he listed components of the mixtures.

A column heading "Ex. 6" or "Ex. 49" means, for example, use of a roportion, which is specified in the appropriate column, of the product from Preparation Example 6 or a random mixture from preparation Example 49.

The additions abbreviated to "Luc", "Irga" and "Daro" in the mixtures are commercially available photoinitiators Lucirin® TPO, Irgacure® 184 and Darocure® 1173. The chemical identity of the additions listed under the other abbreviations is as follows.

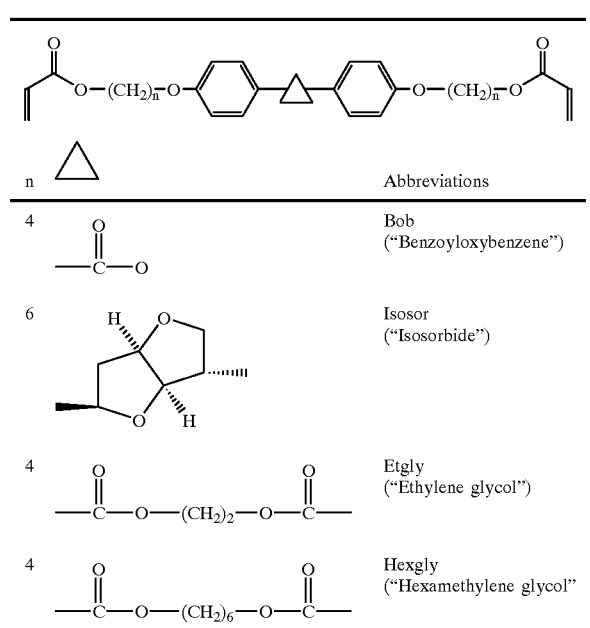

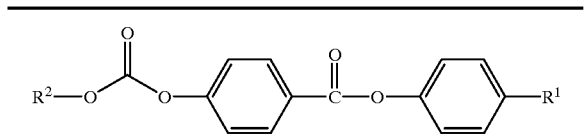

| R¹ | R² | Abbreviation |
|---|---|---|
| —OCH₃ | —C₄H₉ | Bumeox ("Butylmethoxy") |
| —COOC₂H₅ | ⫽ | Vicoxet ("Vinylcarboxylethyl") |
| —COOC₄H₉ | ⫽ | Vicoxbu ("Vinylcarboxylbutyl") |
| —COOC₆H₁₃ | ⫽ | Vicoxhe ("Vinylcarboxylhexyl") |
| —OCH₃ | ⫽ | Vimeox ("Vinylmethoxy") |
| —OCH₃ | ⫽CH₃ | Mevimeox ("Methylvinylmethoxy") |
| —COCH₃ | ⫽ | Vicame ("Vinylcarbonylmethyl") |
| —COC₂H₅ | ⫽ | Vicaet ("Vinylcarbonylethyl") |
| —COC₄H₉ | ⫽ | Vicabu ("Vinylcarbonylbutyl") |
| —C₉H₁₉ | ⫽ | Vinon ("Vinylnonyl") |

TABLE 9

| Mixture | Ex. 2 | Ex. 6 | Ex. 18 | Bob | Phase behavior |
|---|---|---|---|---|---|
| 1 | 85.1 | | | 14.9 | cr 31–64 n 130–138 i |
| 2 | 68.2 | | | 31.8 | cr 32–58 n 110–114 i |
| 3 | 48.8 | | | 51.2 | cr 32–42 n 89–95 i |
| 4 | 38.0 | | | 62.0 | cr 31–46 n 67–71 i |
| 5 | 26.4 | | | 73.6 | cr 32–48 n 70–74 i |
| 6 | | 85.4 | | 14.6 | cr 40–67 n 107–111 i |
| 7 | | 68.7 | | 31.3 | cr 40–54 n 91–96 i |
| 8 | | 49.3 | | 50.7 | cr 35–46 n 72–77 i |
| 9 | 82.9 | | 17.1 | | s 56–64 n 140–142 i |
| 10 | 64.5 | | 35.5 | | s 46–58 n 116–119 i |
| 11 | 54.8 | | 45.2 | | s 46–51 n 98–104 i |
| 12 | 44.7 | | 55.3 | | s 46–49 n 76–80 i |

TABLE 10

| Mixture | Ex. 45 | Ex. 23 | Ex. 30 | Isosor | Bumeox | Luc | Phase behavior |
|---|---|---|---|---|---|---|---|
| 13 | 89.2 | 10.8 | | | | | s 39–40 n 113–119 i |
| 14 | 79.4 | 20.6 | | | | | n 103–105 i |
| 15 | 52.4 | 47.6 | | | | | n 52–55 i |
| 16 | 41.5 | 58.5 | | | | | n 58–61 i |
| 17 | 29.3 | 70.7 | | | | | n 52–55 i |
| 18 | 28.2 | 39.7 | 32.1 | | | | n 62–63 i |
| 19 | 27.4 | 21.2 | 51.4 | | | | n 68–69 i |
| 20 | 58.2 | | | | 41.8 | | s 49–50 n 93–94 i |
| 21 | 30.4 | 55.1 | | | 14.5 | | n 53–55 i |
| 22 | 81.3 | 9.8 | | 8.9 | | | s 40–41 ch 85–93 i |
| 23 | 74.5 | 19.3 | | 6.2 | | | ch 78 i |
| 24 | 72.9 | 18.9 | | 6.1 | | 2.1 | ch 68 i |
| 25 | 72.0 | 18.6 | | 9.4 | | | ch 69–79 i; λ(⊥) = 546 nm |
| 26 | 72.0 | 18.7 | | 7.3 | | 2.0 | ch 75 i |
| 27 | 71.5 | 18.5 | | 10.0 | | | ch 75–80 i |
| 28 | 70.2 | 18.2 | | 9.2 | | 2.4 | ch 60 i; λ(⊥) = 563 nm |
| 29 | 69.8 | 18.1 | | 9.7 | | 2.4 | ch 67–73 i; λ(⊥) = 527 nm |
| 30 | 38.4 | 54.1 | | 7.5 | | | ch 41–46 i |
| 31 | 37.4 | 52.8 | | 7.3 | | 2.5 | ch 31 i |
| 32 | 94.4 | | | 5.6 | | | s 48 ch 112–118 i |
| 33 | 92.1 | | | 5.4 | | 2.5 | s 56 ch 113–118 i |

TABLE 11

| Mixture | Ex. 48 | Ex. 6 | Ex. 18 | Ex. 23 | Isosor | Irga | Luc | Toluene | Phase behavior |
|---|---|---|---|---|---|---|---|---|---|
| 34 | 72.2 | | 27.8 | | | | | | n 116–119 i |
| 35 | 62.6 | | 37.4 | | | | | | n 98–104 i |
| 36 | 52.7 | | 47.3 | | | | | | n 93–98 i |
| 37 | 42.6 | | 57.4 | | | | | | n 76–81 i |
| 38 | 57.9 | | 34.7 | | 7.4 | | | | ch 84–87 i |
| 39 | 55.7 | | 33.3 | | 7.1 | | 3.9 | | red-greed |
| 40 | 55.0 | | 32.9 | | 8.3 | | 3.8 | | green-blue |
| 41 | 86.0 | | | 14.0 | | | | | n 117–123 i |
| 42 | 69.7 | | | 30.3 | | | | | n 98–102 i |
| 43 | 50.6 | | | 49.4 | | | | | n 75–79 i |
| 44 | 45.2 | | | 54.8 | | | | | n 70–73 i |
| 45 | 39.7 | | | 60.3 | | | | | n 64 i |
| 46 | 23.5 | | | 76.5 | | | | | n 43–48 i |
| 47 | 45.3 | 25.1 | | 29.6 | | | | | n 100–104 i |

TABLE 11-continued

| Mixture | Ex. 48 | Ex. 6 | Ex. 18 | Ex. 23 | Isosor | Irga | Luc | Toluene | Phase behavior |
|---|---|---|---|---|---|---|---|---|---|
| 48 | 41.4 | 23.0 | | 27.1 | 8.5 | | | | ch 78–87 i |
| 49 | 46.8 | | | 45.8 | 7.4 | | | | ch 55–67 i |
| 50 | 45.7 | | | 44.6 | 7.2 | | 2.5 | | ch 47 i |
| 51 | 45.0 | | | 44.0 | 7.1 | | 2.4 | 1.5 | ch 48 i; λ(⊥) = 555 nm; flow viscosity: 3 Pa.s |
| 52 | 43.3 | | | 49.2 | 7.5 | | | | ch 56–64 i; λ(⊥) = 539 nm |
| 53 | 41.8 | | | 50.6 | 7.6 | | | | ch 53–60 i |
| 54 | 40.8 | | | 49.4 | 7.4 | | 2.4 | | ch 42–51 i; λ(⊥) = 572 nm |

TABLE 12

| Mixture | Ex. 48 | Ex. 23 | Ex. 24 | Ex. 38 | Isosor | Bob | Luc | Phase behavior |
|---|---|---|---|---|---|---|---|---|
| 55 | 87.6 | 5.1 | | 7.3 | | | | n 109–115 i |
| 56 | 86.9 | 7.7 | | 5.4 | | | | n 110–117 i |
| 57 | 62.7 | 28.6 | | 8.7 | | | | n 72–76 i |
| 58 | 54.5 | 26.6 | | 18.9 | | | | n 44–50 i |
| 59 | 52.4 | 38.5 | | 9.1 | | | | n 60–66 i |
| 60 | 58.0 | 26.5 | | 8.1 | 7.4 | | | ch 49–55 i |
| 61 | 44.5 | 43.5 | | 4.4 | 7.6 | | | ch 46–53 i |
| 62 | 43.4 | 42.4 | | 4.3 | 7.5 | | 2.4 | ch 35 i |
| 63 | 82.7 | | 17.3 | | | | | n 114–119 i |
| 64 | 65.6 | | 34.4 | | | | | n 88–93 i |
| 65 | 46.2 | | 53.8 | | | | | n 59–65 i |
| 66 | 34.7 | | 65.3 | | | | | n 42–49 i |
| 67 | 98.0 | | | 2.0 | | | | n 127–132 i |
| 68 | 84.8 | | | 15.2 | | | | n 81–95 i |
| 69 | 78.2 | | | 21.8 | | | | n 65–76 i; flow viscosity: 3 Pa.s |
| 70 | 70.6 | | | 29.4 | | | | n 41–50 i; flow viscosity: 1.3 Pa.s |
| 71 | 84.1 | | | | | 15.9 | | cr 31–54 n 120–130 i |
| 72 | 66.4 | | | | | 33.6 | | cr 31–61 n 100–109 i |
| 73 | 46.0 | | | | | 54.0 | | cr 31–69 n 80–84 i |
| 74 | 24.8 | | | | | 75.2 | | cr 50 n 67–72 i |

TABLE 13

| Mixture | Ex. 49 | Ex. 23 | Ex. 38 | Ex. 43 | Isosor | Daro | Luc | Toluene | Xylene | Phase behavior |
|---|---|---|---|---|---|---|---|---|---|---|
| 75 | 88.9 | 10.1 | | | | | | | | n 97–99 i; Flow viscosity: 9 Pa.s |
| 76 | 70.4 | 29.6 | | | | | | | | n 79–83 i; Flow viscosity: 5 Pa.s |
| 77 | 50.0 | 50.0 | | | | | | | | n 60–62 i; Flow viscosity: 3 Pa.s |
| 78 | 24.3 | 75.7 | | | | | | | | n 36–42 i; Flow viscosity: 2 Pa.s |
| 79 | 73.7 | 15.4 | 10.9 | | | | | | | n 59–64 i |
| 80 | 73.2 | 20.2 | 6.6 | | | | | | | n 65–70 i |
| 81 | 72.1 | 22.6 | 5.3 | | | | | | | n 68–72 i |
| 82 | 66.5 | 27.7 | | | 5.8 | | | | | ch 67–72 i; red-green |
| 83 | 65.7 | 27.3 | | | 7.0 | | | | | ch 63–69 i; red-green |
| 84 | 65.9 | 27.4 | | | 6.7 | | | | | ch 65 i |
| 85 | 64.6 | 26.9 | | | 9.5 | | | | | ch 57 i |
| 86 | 47.9 | 44.8 | | | 7.3 | | | | | ch 46–54 i |
| 87 | 63.0 | 26.2 | | | 6.4 | | 2.4 | | 2.0 | ch 57 i; λ(⊥) = 704 nm |
| 88 | 61.2 | 25.5 | | | 8.0 | | 2.4 | 2.9 | | ch 50 i; λ(⊥) = 533 nm; flow viscosity: 3 Pa.s |
| 89 | 61.3 | 25.5 | | | 8.0 | 3.7 | 1.5 | | | ch 42 i; λ(⊥) = 533 nm; flow viscosity: 3 Pa.s |
| 90 | 60.8 | 25.3 | | 3.5 | 8.0 | 2.4 | | | | ch 44 i |

TABLE 14

| Mixture | Ex. 49 | Ex. 24 | Ex. 28 | Ex. 29 | Ex. 31 | Ex. 32 | Ex. 33 | Phase behavior |
|---|---|---|---|---|---|---|---|---|
| 91 | 86.7 | 13.3 | | | | | | n 95–99 i |
| 92 | 71.4 | 28.6 | | | | | | n 75–80 i |
| 93 | 52.6 | 47.3 | | | | | | n 54–76 i |
| 94 | 29.4 | 70.6 | | | | | | n 29–32 i |
| 95 | 86.2 | | 13.8 | | | | | n 106–121 i |
| 96 | 69.0 | | 31.0 | | | | | n 92–106 i |
| 97 | 49.7 | | 50.3 | | | | | cr 52 n 77–92 i |
| 98 | 85.2 | | | 14.8 | | | | n 106–119 i |
| 99 | 77.6 | | | 22.4 | | | | n 99–104 i; flow viscosity: 10.6 Pa.s |
| 100 | 68.3 | | | 31.7 | | | | n 98–112 i |
| 101 | 58.1 | | | 41.9 | | | | n 85–87 i; flow viscosity: 10.6 Pa.s |
| 102 | 48.9 | | | 51.1 | | | | n 88–101 i |
| 103 | 37.2 | | | 62.8 | | | | n 72–75 i |
| 104 | 84.3 | | | | 15.7 | | | n 102–104 i |
| 105 | 63.6 | | | | 36.4 | | | n 69–72 i |
| 106 | 40.7 | | | | 59.3 | | | n 34–55 |
| 107 | 78.7 | | | | | 21.3 | | n 98–103 i |
| 108 | 66.6 | | | | | 33.4 | | n 79–83 i |
| 109 | 77.6 | | | | | | 22.4 | n 88–91 i |
| 110 | 59.5 | | | | | | 40.5 | n 59–63 i |

TABLE 15

| Mixture | Ex. 49 | Ex. 34 | Ex. 35 | Ex. 36 | Ex. 37 | Ex. 38 | Ex. 38 | Ex. 39 | Phase behavior |
|---|---|---|---|---|---|---|---|---|---|
| 111 | 81.2 | 19.8 | | | | | | | n 91–93 i |
| 112 | 65.6 | 34.4 | | | | | | | n 69–73 i |
| 113 | 40.9 | 59.1 | | | | | | | n 36–38 i |
| 114 | 80.8 | | 19.2 | | | | | | n 89–92 i |
| 115 | 58.3 | | 41.2 | | | | | | n 55–61 i |
| 116 | 79.8 | | | 20.2 | | | | | n 103–106 i; flow viscosity: 15.7 Pa.s |
| 117 | 73.7 | | | 26.3 | | | | | n 87–90 i; flow viscosity: 11.7 Pa.s |
| 118 | 50.8 | | | 49.2 | | | | | n 67–69 i; flow viscosity: 10.6 Pa.s |
| 119 | 81.1 | | | | 18.9 | | | | n 97–100 i |
| 120 | 59.0 | | | | 41.0 | | | | n 74–77 i |
| 121 | 40.4 | | | | 59.6 | | | | n 53–57 i |
| 122 | 95.8 | | | | | 4.2 | | | n 96–99 i |
| 123 | 75.2 | | | | | 24.8 | | | n 34–43 i; flow viscosity: 1.3 Pa.s |
| 124 | 79.1 | | | | | | 20.9 | | n 68–70 i |
| 125 | 76.2 | | | | | | | 23.8 | n 59–65 i |

TABLE 16

| Mixture | Ex. 49 | Etgly | Hexgly | Vicoxet | Vicoxbu | Vicoxhe | Vimeox | Phase behavior |
|---|---|---|---|---|---|---|---|---|
| 126 | 82.8 | 17.2 | | | | | | n 75–81 i |
| 127 | 77.3 | | 22.7 | | | | | n 67–73 i |
| 128 | 80.0 | | | 20.0 | | | | n 109–111 i |
| 129 | 75.0 | | | 25.0 | | | | n 91–93 i |
| 130 | 59.3 | | | 40.7 | | | | n 97–100 i |
| 131 | 57.4 | | | 42.6 | | | | n 69–72 i |
| 132 | 47.7 | | | 52.3 | | | | n 92–95 i |
| 133 | 43.6 | | | 56.4 | | | | n 56–59 i |
| 134 | 80.8 | | | | 19.2 | | | n 101–103 i |
| 135 | 59.3 | | | | 40.7 | | | n 79–82 i |
| 136 | 38.0 | | | | 62.0 | | | n 56–58 i |
| 137 | 79.5 | | | | | 20.5 | | n 99–101 i |
| 138 | 59.9 | | | | | 40.1 | | n 68–71 i |
| 139 | 89.4 | | | | | | 10.6 | n 112–115 i |
| 140 | 76.0 | | | | | | 24.0 | n 108–119 i |

TABLE 16-continued

| Mixture | Ex. 49 | Etgly | Hexgly | Vicoxet | Vicoxbu | Vicoxhe | Vimeox | Phase behavior |
|---|---|---|---|---|---|---|---|---|
| 141 | 58.4 | | | | | | 41.6 | cr 57 n 105–117 i |

TABLE 17

| Mixture | Ex. 49 | Mevimeox | Vicame | Vicaet | Vicabu | Vinon | Phase behavior |
|---|---|---|---|---|---|---|---|
| 142 | 89.0 | 11.0 | | | | | n 111–124 i |
| 143 | 75.1 | 24.9 | | | | | n 103–115 i |
| 144 | 57.3 | 42.7 | | | | | cr 55 n 91–102 i |
| 145 | 89.0 | | 11.0 | | | | n 115–133 i |
| 146 | 75.3 | | 24.7 | | | | n 119–132 i |
| 147 | 57.6 | | 42.4 | | | | n 118–131 i |
| 148 | 88.6 | | | 11.4 | | | n 120–130 i |
| 149 | 74.5 | | | 25.5 | | | n 123–131 i |
| 150 | 56.5 | | | 43.5 | | | n 130–135 i |
| 151 | 88.7 | | | | 11.3 | | n 114–126 i |
| 152 | 74.6 | | | | 25.4 | | n 110–121 i |
| 153 | 56.6 | | | | 43.4 | | cr 58 n 111–119 i |
| 154 | 86.5 | | | | | 13.5 | n 82–106 i |

We claim:

1. A polymerizable liquid-crystalline compound of the formula I $$Z^1-Y^1-A^1-Y^3-M-Y^4-A^2-Y^2-Z^2 \quad \text{I}$$

where $Z^1$ and $Z^2$ are radicals containing reactive groups via which polymerization can be effected, $Y^1-Y^4$ are a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups $Y^3$ and $Y^4$ is —O—CO—O—, —O—CO—NR—, —NR—CO—O— or —NR—CO—NR—, $A^1$ and $A^2$ are spacers having 2 to 30 carbon atoms in which the carbon chain may be interrupted by ether oxygen, thioether sulfur or by nonadjacent imino or $C_1$–$C_4$-alkylimino groups, M is a mesogenic group, R is $C_1$–$C_4$-alkyl.

2. A polymerizable liquid-crystalline compound as claimed in claim 1, where at least one of the groups $Y^3$ and $Y^4$ is —O—CO—O—.

3. A polymerizable liquid-crystalline compound as claimed in claim 1, where the mesogenic group M is a group of the formula Ia $$-(-T-Y^5-)_r-T-\quad \text{Ia}$$

where

T is a divalent saturated or unsaturated iso- or heterocyclic radical, $Y^5$ is a radical as defined for $Y^1$–$Y^4$ or is —O—CH$_2$—, —CH$_2$—O—, —CH=N—, —N=CH— or —N=N—, r is 0, 1, 2 or 3, where the radicals T and $Y^5$, in the case where r is >0, may be identical or different.

4. A polymerizable liquid-crystalline compound as claimed in claim 1, where the mesogenic group M is a group of the following formulae

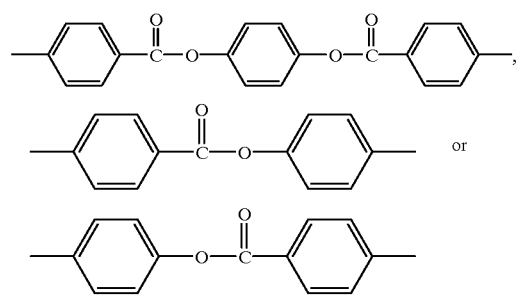

where each ring can carry up to three identical or different substituents from the following group:

$C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbonyloxy, $C_1$–$C_{20}$-alkylcarbonylamino, formyl, halogen, cyano, hydroxyl and nitro.

5. A polymerizable liquid-crystalline compound as claimed in claim 1, where the radical pairs $Z^1$ and $Z^2$, $Y^1$ and $Y^2$, $Y^3$ and $Y^4$, and $A^1$ and $A^2$ are in each case identical.

6. A liquid-crystal composition comprising a) at least one compound as claimed in claim 1, which is optionally mixed with b) one or more compounds of the formula II $$Z^3-Y^6-A^3-Y^7-M-Y^8-P^1 \quad \text{II,}$$

where $Z^3$ is a radical containing reactive groups via which polymerization can be effected, $Y^6-Y^8$ are a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups $Y^7$ and $Y^8$ is —O—CO—O—, —O—CO—NR—, —NR—CO—O or —NR—CO—NR—, $A^3$ is a spacer having 2 to 30 carbon atoms in which the carbon chain may be interrupted by ether oxygen, thioether sulfur or by nonadjacent imino or $C_1$–$C_4$-alkylimino groups, P$^1$ is a radical selected from the group of hydrogen, C$_1$–C$_{30}$-alkyl, C$_1$–C$_{30}$-acyl, C$_3$–C$_8$-cycloalkyl unsubstituted or substituted by one to three C$_1$–C$_6$-alkyl and where the carbon chain of the alkyl, acyl and cycloalkyl radicals may be interrupted by ether oxygen, thioether sulfur or by nonadjacent imino or C$_1$–C$_4$-alkylimino groups, and/or c) one or more compounds of the formula III $$P^2-Y^9-M-Y^{10}-P^3 \qquad \text{III,}$$

where

P$^2$, P$^3$ are radicals selected from the group of hydrogen, C$_1$–C$_{30}$-alkyl, C$_1$–C$_{30}$-acyl, C$_3$–C$_8$-cycloalkyl unsubstituted or substituted by one to three C$_1$–C$_6$-alkyl, and where the carbon chain of the alkyl, acyl and cycloalkyl radicals may be interrupted by ether oxygen, thioether sulfur or by nonadjacent imino or C$_1$–C$_4$-alkylimino groups, Y$^9$, Y$^{10}$ are a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups Y$^9$ and Y$^{10}$ is —O—CO—O—, —O—CO—NR—, —NR—CO—O or —NR—CO—NR—, M is a mesogenic group, where the mesogenic groups M of the formulae I, II and III can be identical to or different from one another.

7. A liquid-crystal composition comprising one or more compounds of the formulae I, II and III as claimed in claim 6 and one or more chiral compounds.

8. A liquid-crystal composition as claimed in claim 6, comprising components a), b) and c) in a molar proportion based on the total amount of said components of
a) 1–98 mol %.
b) 1–98 mol %,
c) 0.01–90 mol %,
with the proviso that the total of the mol % of the components is 100 mol %.

9. A liquid-crystal composition as claimed in claim 7, comprising components a), b) and c) in a proportion of from 60 to 99.999% by weight and the chiral compound or chiral compounds in a proportion of from 0.001 to 40% by weight, in each case based on the total amount of components a), b) and c), and of the chiral compound or chiral compounds, with the proviso that the total of the percent by weight of the compounds is 100% by weight.

10. A liquid-crystal composition comprising 10 to 100% by weight of the polymerizable liquid-crystalline compounds I, I and II and/or III as claimed in claim 6, 0 to 90% by weight of other monomers and 0 to 50% by weight of one or more chiral compounds, in each case based on the total weight of the liquid-crystal composition.

11. A process for preparing one or more polymerizable liquid-crystalline compounds of the formula I from claim 1, where the two variables Y$^3$ and Y$^4$ are both —O—CO—O—, which comprises reacting one or more chloroformates of the formula IVa $$Z^1-Y^1-A^1-O-CO-Cl \qquad \text{IVa}$$

with one or more mesogen diols of the formula V $$HO-M-OH \qquad \text{V}$$

to give the symmetrical compound of the formula Ia $$Z^1-Y^1-A^1-O-CO-O-M-O-CO-O-A^1-Y^1-Z^1 \qquad \text{Ia}$$

or reacting in a first step a chloroformate of the formula IVa and in a second step a chloroformate of the formula IVb $$Z^2-Y^2-A^2-O-CO-Cl \qquad \text{IVb}$$

with a mesogen diol of the formula V to give the asymmetrical compound Ib $$Z^1-Y^1-A^1-O-CO-O-M-O-CO-O-A^2-Y^2-Z^2 \qquad \text{Ib.}$$

12. A liquid-crystalline compound of the formula II $$Z^3-Y^6-A^3-Y^7-M-Y^8-P^1 \qquad \text{(II),}$$

where

Z$^3$ is a radical containing reactive groups via which polymerization can be effected, Y$^6$ is oxygen, sulfur, —O—CO—, —CO—O—, —O—CO—O—, —CO—NR—, —NR—CO—, —O—CO—NR—, —NR—CO—O— or —NR—CO—NR—, Y$^7$ and Y$^8$ are each a single chemical bond, oxygen, sulfur, —O—CO—, —CO—O—, —O—CO—O—, —CO—NR—, —NR—CO—, —O—CO—NR—, —NR—CO—O— or —NR—CO—NR—, where at least one of the groups Y$^7$ and Y$^8$ is —O—CO—O—, —O—CO—NR—, —NR—CO—O— or —NR—CO—NR—, A$^3$ is a spacer having 2 to 30 carbon atoms in which the carbon chain may be interrupted by ether oxygen, thioether, sulfur or by nonadjacent imino or C$_1$–C$_4$-alkylimino groups, P$^1$ is a radical selected from the group consisting of hydrogen, C$_1$–C$_{30}$-alkyl, C$_1$–C$_{30}$-acyl, C$_3$–C$_8$-cycloalkyl unsubstituted or substituted by one to three C$_1$–C$_6$-alkyl and where the carbon chain of the alkyl, acyl and cycloalkyl radicals may be interrupted by ether oxygen, thioether sulfur or by nonadjacent imino or C$_1$–C$_4$-alkylimino groups, M is a mesogenic group, and R is a C$_1$–C$_4$ alkyl group.

13. A process for preparing one or more liquid-crystalline compounds of the formula II from claim 12, where the two variables Y$^7$ and Y$^8$ are both —O—CO—O—, which comprises reacting in a first step a chloroformate of the formula IVc $$Z^3-Y^6-A^3-O-CO-Cl \qquad \text{IVc}$$

or a chloroformate of the formula VI $$P^1-O-CO-Cl \qquad \text{VI}$$

and in a second step a chloroformate of the formula VI or a chloroformate of the formula IVc with one or more mesogen diols of the formula V $$HO-M-OH \qquad \text{V.}$$

14. A process as claimed in claim 11, wherein the reaction is carried out in the presence of an organic and/or inorganic base.

15. A process for producing coatings having a liquid-crystalline ordered state, which comprises applying one or more liquid-crystalline compounds as claimed in claim 1 and, optionally, further polymerizable compounds and chiral compounds to a substrate, effecting a liquid-crystalline alignment, and then polymerizing the compounds applied to the substrate.

16. A coated article obtainable by a process as claimed in claim 15.

17. A cholesteric liquid-crystalline colorant comprising a liquid-crystal composition as claimed in claim 7.

18. A pigment obtainable by subjecting a liquid-crystal composition as claimed in claim 7 to polymerization and then comminuting the polymeric material to a pigment particle size.

19. The polymerizable liquid-crystalline compound of the formula I of claim 1, wherein $Z^1$ and $Z^2$ are independently selected from the following groups:

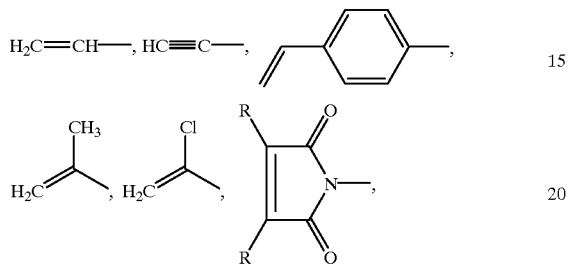

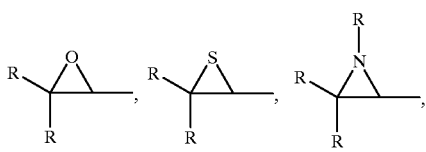

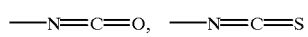

and

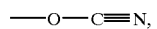

* * * * *